US009815863B2

(12) United States Patent
Pereira

(10) Patent No.: US 9,815,863 B2
(45) Date of Patent: Nov. 14, 2017

(54) HYDROGEN BOND FORMING FLUORO KETOLIDES FOR TREATING DISEASES

(75) Inventor: David E. Pereira, Apex, NC (US)

(73) Assignee: CEMPRA PHARMACEUTICALS, INC., Chapel Hill, NC (US)

(*) Notice: Subject to any disclaimer, the term of this patent is extended or adjusted under 35 U.S.C. 154(b) by 0 days.

(21) Appl. No.: 13/821,314

(22) PCT Filed: Sep. 9, 2011

(86) PCT No.: PCT/US2011/051064
§ 371 (c)(1),
(2), (4) Date: Mar. 7, 2013

(87) PCT Pub. No.: WO2012/034058
PCT Pub. Date: Mar. 15, 2012

(65) Prior Publication Data
US 2013/0172280 A1 Jul. 4, 2013

Related U.S. Application Data

(60) Provisional application No. 61/381,794, filed on Sep. 10, 2010.

(51) Int. Cl.
C07H 17/08 (2006.01)
A61K 31/7048 (2006.01)
A61K 31/7056 (2006.01)
C07D 498/04 (2006.01)

(52) U.S. Cl.
CPC ............ C07H 17/08 (2013.01); C07D 498/04 (2013.01)

(58) Field of Classification Search
CPC ...................................... C07H 17/08
USPC ............................................ 536/7.4
See application file for complete search history.

(56) References Cited

U.S. PATENT DOCUMENTS

| | | | |
|---|---|---|---|
| 1,354,753 A | 10/1920 | Howard | |
| 2,180,006 A | 11/1939 | Hasche | |
| 3,668,282 A | 6/1972 | Below | |
| 3,843,787 A | 10/1974 | Fabrizio | |
| 4,312,866 A | 1/1982 | Caruso | |
| 4,331,803 A | 5/1982 | Watanabe | |
| 4,474,768 A | 10/1984 | Bright | |
| 4,742,049 A | 5/1988 | Baker | |
| 4,886,792 A | 12/1989 | Djokic | |
| 4,990,602 A | 2/1991 | Morimoto | |
| 5,211,955 A | 5/1993 | Legros | |
| 5,444,051 A | 8/1995 | Agouridas | |
| 5,527,780 A * | 6/1996 | Agouridas | ............... C07H 17/08 514/29 |
| 5,543,400 A | 8/1996 | Agouridas | |
| 5,614,614 A * | 3/1997 | Agouridas | ............... C07H 17/00 536/7.2 |
| 5,635,485 A | 6/1997 | Agouridas | |
| 5,656,607 A | 8/1997 | Agouridas | |
| 5,747,467 A | 5/1998 | Agouridas | |
| 5,760,233 A | 6/1998 | Agouridas | |
| 5,770,579 A | 6/1998 | Agouridas | |
| 5,834,428 A | 11/1998 | Drucker | |
| 5,985,844 A | 11/1999 | Heck | |
| 6,011,142 A | 1/2000 | Bonnet | |
| 6,020,521 A | 2/2000 | Randolph | |
| 6,028,181 A | 2/2000 | Or | |
| 6,096,714 A | 8/2000 | Agouridas | |
| 6,096,922 A | 8/2000 | Lal | |
| 6,121,432 A | 9/2000 | Bonnet | |
| 6,270,768 B1 | 8/2001 | OConnell | |
| 6,313,101 B1 * | 11/2001 | Denis | ..................... C07H 17/08 514/29 |
| 6,395,300 B1 | 5/2002 | Liang | |
| 6,395,710 B1 | 5/2002 | Chu | |
| 6,407,074 B1 | 6/2002 | Bronk | |
| 6,407,257 B1 * | 6/2002 | Agouridas et al. | ........ 548/335.1 |
| 6,420,535 B1 | 7/2002 | Phan | |
| 6,437,106 B1 | 8/2002 | Stoner | |
| 6,440,941 B1 * | 8/2002 | Denis | .............. 514/29 |
| 6,455,505 B2 | 9/2002 | Agouridas | |
| 6,515,116 B2 | 2/2003 | Suh | |
| 6,555,524 B2 | 4/2003 | Kaneko | |
| 6,664,238 B1 | 12/2003 | Su | |
| 6,777,393 B2 | 8/2004 | Bronk | |
| 6,809,188 B1 | 10/2004 | Suh | |
| 6,849,608 B2 | 2/2005 | Su | |
| 6,890,907 B2 | 5/2005 | Speirs | |
| 7,163,924 B2 * | 1/2007 | Burger et al. | ................... 514/29 |

(Continued)

FOREIGN PATENT DOCUMENTS

| | | |
|---|---|---|
| CN | 1354753 | 6/2002 |
| CN | 101045063 | 10/2007 |

(Continued)

OTHER PUBLICATIONS

Organic Compounds Crystal Manufacture Handbook—Principles and Knowhow, 2008, pp. 57-84.

Baker, William R., et al. "Modification of macrolide antibiotics. Synthesis of 11-deoxy-11-(carboxyamino)-6-O-methylerythromycin A 11, 12-(cyclic esters) via an intramolecular Michael reaction of O-carbamates with an. alpha.,. beta.-unsaturated ketone." The Journal of Organic Chemistry 53.10 (1988): 2340-2345.

Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.

Champney et al., 'Structure-Activity Relationships for Six Ketolide Antibiotics', Current Microbiology, 42:203-10 (2001).

(Continued)

Primary Examiner — Layla Berry
(74) Attorney, Agent, or Firm — Brannon Sowers & Cracraft PC

(57) ABSTRACT

The invention described herein pertains to a novel macrolide antibacterial agent of formula (I): A-L-Q, as defined herein, and pharmaceutically acceptable salts, solvates, and hydrates thereof. Inter alia, the new macrolide antibacterial agent is active against a number of bacterial species, including resistant species.

31 Claims, No Drawings

(56) References Cited

U.S. PATENT DOCUMENTS

| | | |
|---|---|---|
| 7,332,476 B2 | 2/2008 | Burger |
| 7,375,234 B2 | 5/2008 | Sharpless |
| 7,419,961 B2 | 9/2008 | Napoletano |
| 7,601,695 B2 | 10/2009 | Liang |
| 8,247,394 B2 | 8/2012 | Fernandes |
| 8,791,080 B2 | 7/2014 | Fernandes |
| 8,796,232 B2 | 8/2014 | Fernandes |
| 9,051,346 B2 | 6/2015 | Pereira |
| 2002/0028781 A1 | 3/2002 | Agouridas |
| 2002/0044967 A1 | 4/2002 | Yamashita |
| 2003/0143162 A1 | 7/2003 | Speirs |
| 2003/0176327 A1 | 9/2003 | Cassell |
| 2004/0009930 A1 | 1/2004 | Su |
| 2004/0014685 A1 | 1/2004 | Mercep |
| 2005/0009764 A1 | 1/2005 | Burger et al. |
| 2005/0014706 A1 | 1/2005 | Falzari |
| 2005/0022242 A1 | 1/2005 | Rosetti |
| 2005/0153905 A1 | 7/2005 | Burger |
| 2005/0209172 A1 | 9/2005 | Woo |
| 2005/0222427 A1 | 10/2005 | Sharpless |
| 2006/0100164 A1* | 5/2006 | Liang et al. ............. 514/28 |
| 2006/0264385 A1 | 11/2006 | Wang |
| 2007/0015719 A1 | 1/2007 | Jenkins |
| 2007/0167382 A1 | 7/2007 | Finkelstein |
| 2007/0197518 A1 | 8/2007 | Johnson |
| 2007/0281894 A1 | 12/2007 | Gant |
| 2008/0113926 A1 | 5/2008 | Ivezic |
| 2008/0221048 A1 | 9/2008 | Woo |
| 2008/0227730 A1 | 9/2008 | Mutak |
| 2008/0241959 A1 | 10/2008 | Culic |
| 2008/0287376 A1 | 11/2008 | Das |
| 2009/0075916 A1 | 3/2009 | Upadhyay |
| 2009/0076253 A1 | 3/2009 | Kashimura |
| 2009/0087389 A1 | 4/2009 | Leonard |
| 2009/0156517 A1 | 6/2009 | Zhang |
| 2010/0216731 A1 | 8/2010 | Pereira |
| 2011/0195920 A1 | 8/2011 | Fernandes |
| 2012/0071429 A1 | 3/2012 | Duffield |
| 2012/0172323 A1 | 7/2012 | Fernandes |
| 2013/0011453 A1 | 1/2013 | Latta |
| 2013/0018008 A1 | 1/2013 | Pereira |
| 2013/0045937 A1 | 2/2013 | Pereira |
| 2013/0053362 A1 | 2/2013 | Castro |
| 2013/0156705 A1 | 6/2013 | Zhang |
| 2013/0164351 A1 | 6/2013 | Fernandes |
| 2013/0172280 A1 | 7/2013 | Pereira |
| 2013/0345410 A1 | 12/2013 | Liang |
| 2014/0088062 A1 | 3/2014 | Pereira |
| 2014/0148431 A1 | 5/2014 | Patel |

FOREIGN PATENT DOCUMENTS

| | | |
|---|---|---|
| EP | 0248279 A2 | 12/1987 |
| EP | 0680967 A1 | 11/1995 |
| EP | 1024145 A2 | 8/2000 |
| EP | 1167375 | 1/2002 |
| GB | 891817 | 3/1962 |
| JP | 06220082 | 8/1994 |
| JP | 08053489 | 2/1996 |
| JP | 2000507573 | 6/2000 |
| JP | 2000229993 | 8/2000 |
| JP | 2000351794 | 12/2000 |
| JP | 2002514197 | 5/2002 |
| JP | 2004502736 | 1/2004 |
| JP | 2006528667 | 12/2006 |
| JP | 2007536371 | 12/2007 |
| JP | 2008519788 | 6/2008 |
| JP | 2008526948 | 7/2008 |
| JP | 2008534504 | 8/2008 |
| JP | 2009500356 | 1/2009 |
| JP | 2009502788 | 1/2009 |
| JP | 5914335 | 5/2016 |
| RU | 2230748 | 6/2004 |
| WO | 9736912 | 10/1997 |
| WO | 9830574 A1 | 7/1998 |
| WO | 9856800 A1 | 12/1998 |
| WO | 9921866 A1 | 5/1999 |
| WO | 9928311 A1 | 6/1999 |
| WO | 0012521 A1 | 3/2000 |
| WO | 0031099 A1 | 6/2000 |
| WO | 0044761 A2 | 8/2000 |
| WO | 0062783 A2 | 10/2000 |
| WO | 0110878 | 2/2001 |
| WO | 0110878 A1 | 2/2001 |
| WO | 0250092 A1 | 6/2002 |
| WO | 03004509 | 1/2003 |
| WO | 03004509 A2 | 1/2003 |
| WO | 03072141 A1 | 9/2003 |
| WO | 2004080391 A2 | 9/2004 |
| WO | 2004101587 | 11/2004 |
| WO | 2005074945 | 8/2005 |
| WO | 2005105821 | 11/2005 |
| WO | 2005108412 | 11/2005 |
| WO | 2006050941 | 5/2006 |
| WO | 2006050942 | 5/2006 |
| WO | 2006087642 | 8/2006 |
| WO | 2007008537 | 1/2007 |
| WO | 2007059307 A2 | 5/2007 |
| WO | 2007060627 | 5/2007 |
| WO | 20070143507 | 12/2007 |
| WO | 2009055557 | 4/2009 |
| WO | 2009055557 A1 | 4/2009 |
| WO | 2010048599 | 4/2010 |
| WO | 2010048600 | 4/2010 |
| WO | 2010048601 | 4/2010 |
| WO | 2011008193 | 1/2011 |
| WO | 2011032052 | 3/2011 |
| WO | 2011112864 A1 | 9/2011 |
| WO | 2011119604 | 9/2011 |
| WO | 2011146829 | 11/2011 |
| WO | 2012042534 | 4/2012 |
| WO | 2013148891 | 10/2013 |
| WO | 2014145210 | 9/2014 |
| WO | 2014152326 | 9/2014 |
| WO | 2014165792 | 10/2014 |
| WO | 2015181723 | 12/2015 |

OTHER PUBLICATIONS

Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).

Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).

LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.

Or et al., 'Design, Synthesis, and Antimicrobial Activity of 6-0-Substituted Ketolides Active Against Resistant Respiratory Tract Pathogens', J. Med. Chem., 43:1045-49 (2000).

Phan, L.T. et al., 'Synthesis of 2-Fluoro-6-O-propargy1-11,12-carbamate Ketolides. A Novel Class of Antibiotics,' Org. Ltrs., 2:2951-2954 (2000).

Physicians' Desk Reference, p. 2905, (2007).

Romero et al., 'An efficient entry to new sugar modified ketolide antibiotics' Tetrahedron Letters, vol. 46, 2005, pp. 1483-1487.

Torne et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 67:3057-64 (2002).

Vince, R., Almquist, R. G., Ritter, C. L., and Daluge, S., Antimicrobial Agents and Chemotherapy, vol. 8, No. 4, 1975, 439-443.

Celebuski, J.E. et al., 'Chemical Modification of Erythromycin: Novel Reaction Observed by Treatment with Metalloporphyrins', vol. 35, No. 23, pp. 3837-3850, 1994, Elsevier Science Ltd.

Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.

(56) References Cited

OTHER PUBLICATIONS

Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.

Barcia-Macay, Maritza, et al., 'Pharmacodynamic Evaluation of the Intracellular Activities of Antibiotics Against*Staphylococcus aureus* in a Model of THP-1 Macrophages', 2006, Antimicrobial Agents and Chemotherapy. vol. 50, No. 3, pp. 841-851.

Bebear, C.M., et al., In vitro activity of trovafloxacin compared to those of five antimicrobials against mycoplasmas including Mycoplasma hominis and Ureaplasma urealyticum fluoroquinolone-resistant isolates that have been genetically characterized, Antimicrob Agents Chemother 44:2557-2560 (2000).

Berge, Stephen M., et al., "Pharmaceutical Salts", 1977, Journal of Pharmaceutical Sciences, vol. 66, No. 1, pp. 1-19.

Bermudez, Luiz E., et al., "EDP-420, a Bicyclolide (Bridged Bicyclic Macrolide), Is Active Against *Mcyobacterium avium*", 2007, Antimicrobal Agents and Chemotherapy, vol. 51, No. 5, pp. 1666-1670.

Bermudez, Luiz E., et al., "Telithromycin is Active Against*Mycobacterium avium* in Mice Despite Lacking Significant Activity in Standard in Vitro and Macrophage Assays and Is Associated with Low Frequency of Resistance During Treatment", 2001, Antimicrobal Agents and Chemotherapy, vol. 45, No. 8, pp. 2210-2214.

Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp. 799-800.

Cynamon, M. H., et al., "Activity of ABT-773 Against*Mycobacterium avium* Complex in the Beige Mouse Model", 2000, Antimicrobal Agents and Chemotherapy, vol. 44, No. 10, pp. 2895-2896.

Drusano, G. L., et al., "Is 60 Days of Ciprofloxacin Adminstration Necessary for Postexposure Prophylaxis for Bacillus Anthracis?", 2008, Antimicrobial Agents and Chemotherapy. vol. 52, No. 11, pp. 3973-3979.

Duffy, L., et al., Fluoroquinolone resistance in Ureaplasma parvum in the United States, J Clin Microbiol 44:1590-1591 (2006).

European Search Report for EP 09 82 2827, dated Mar. 21, 2012.

Feder, P. I., et al., 1991. Statistical Analysis of Dose-Response Experiments by Maximum Likelihood Analysis and Iteratively Reweighted Nonlinear Least Squares Regression Techniques, 1991, Drug Information Journal, vol. 28, pp. 323-334.

Holzer, G., et al., "Kα1,2 and Kβ1,3 X-Ray Emission Lines of the 3d Transition Metals", Dec. 1997, Physical Review, vol. 56, No. 6, pp. 4554-4568.

Inglesby, Thomas V., et al., "Anthrax as a Biological Weapon, 2002", 2002, Journal of the American Medical Association, vol. 287, No. 17, pp. 2236-2252.

International Search Report for PCT/US2009/061977, dated Dec. 23, 2009, (3 pages).

International Search Report Written Opinion for PCT/US2008/080936 dated Dec. 8, 2008.

Jensen, J.S., et al., Azithromycin Treatment Failure in Mycoplasma genitaliumPositive Patients with Nongonococcal Urethritis Is Associated with Induced Macrolide Resistance, Clin Infect Dis 47:1546-53 (2008).

Jones et al.: 'MIC Quality Control Guidelines and Disk Diffusion Test Optimization for CEM-101, a Novel Fluoroketolide' Journal of Clinical Microbiology vol. 48, No. 4, Dec. 30, 2009, pp. 1470-1473.

Laine, Loren, et al., "Prospective comparison of H&E, Giemsa and Genta stains for the diagnosis of Helicobacter pylori," 1997, Gastrointestinal Endoscopy, vol. 45, No. 6, pp. 463-467.

Lee, Adrian, et al., "A standard mouse model of Helicobacter pylori infection: introducing the Sydney Strain," 1997, Gastroenterology, vol. 112, pp. 1386-1397.

Lemaire, Sandrine, et al., "Cellular Accumulation and Pharmacodynamic Evaluation of the Intracellular Activity of CEM-101, a Novel Fluoroketolide, Against *Staphylococcus aureus*, *Listeria monocytogenes* and *Legionella pneumophila* in Human THP-1 Macrophages", 2009, Antimicrobial Agents and Chemotherapy. vol. 53, No. 9, pp. 3734-3743.

Li, X., et al., Emerging macrolide resistance in Mycoplasma pneumoniae in children: detection and characterization of resistant isolates, Pediatr Infect Dis J, 28:693-696 (2009).

Liang C. H. et al., 'Synthesis and biological activity of new 5-0-sugar modified ketolide and 2-fluoro-ketolide antibiotics,' Bioorganic & Medicinal Chemistry Letters, Pergamon, Elsevier Science, GB, vol. 15, No. 5, Mar. 1, 2005, pp. 1307-1310.

Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.

Patel, Ramesh N., "Stereoselective Biocatalysis", 2000, Bristol-Myers Squibb Research Institute; pp. 775-797.

PCT International Search Report and Written Opinion for PCT/US2011/029424, dated May 25, 2011.

PCT Search Report/Written Opinion prepared for PCT/US2010/048540, dated Oct. 21, 2010.

PCT Search Report and Written Opinion for PCT/US2011/037330 dated Aug. 26, 2011.

PCT Search Report and Written Opinion prepared for PCT/US2009/061978 dated Dec. 9, 2009.

Plata et al., "The synthesis of ketolide antibiotic ABT-773 (cethromycin)," Tetrahedron.

Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).

Vennerstrom, Jonathan L., et al., "Identification of an Antimalarial Synthetic Trioxolane Drug Development Candidate", 2004, Letters to Nature, vol. 430, pp. 900-904.

Waites, K.B., et al., Mycoplasmas and ureaplasmas as neonatal pathogens, Clin Microbiol Rev 18:757-89 (2005).

Zhenkun Ma & Peter A. Nemoto "Discovery and Development of Ketolides as a New Generation of MacrolideAntimicrobial Agents" Curr Med Chem-Anti-Infective Agents 1:15-34 (2002).

Zuckerman, "Macrolides and ketolides: azithromycin, clarithromycin, telithromycin", Infectious Disease Clinics of North America, vol. 18, (2004), pp. 621-649.

Caira MR, "Crystalline polymorphism of orgainic compounds," Design of Organic Solids, Topics in Current Chemistry, Springer Berlin Heidelberg, 1998, pp. 163-208.

Pathak et al., "Enzymatic Protecting Group Techniques in Organic Synthesis," Stereosel, Biocatal., 2000; pp. 775-797.

Katz, Leonard, and Gary W. Ashley. "Translation and protein synthesis: macrolides." Chemical reviews 105.2 (2005): 499-528.

Threlfall, Terence L. "Analysis of organic polymorphs. A review." Analyst 120.10 (1995): 2435-2460.

Petit, Samuel, and Gérard Coquerel. "The amorphous state." Polymorphism: In the Pharmaceutical Industry 10 (2006): 1.

Hancock, Bruno C., Sheri L. Shamblin, and George Zografi. "Molecular mobility of amorphous pharmaceutical solids below their glass transition temperatures." Pharmaceutical research 12.6 (1995): 799-806.

Ashizawa, Kazuhide, "Physico-Chemical Studies on the Molecular Details of Drug Crystals," Phar Tech Japan, 2002, vol. 18, No. 10, pp. 81-96.

Byrn, S., Pfeiffer, R., Ganey, M., Hoiberg, C., & Poochikian, G. (1995). Pharmaceutical solids: a strategic approach to regulatory considerations. Pharmaceutical research, 12(7), 945-954.

Sumerkan, B., Aygen, B., Doganay, M., & Sehmen, E. (1996). Antimicrobial susceptibility of Bacillus anthracis against macrolides. Salisbury Med Bull Supplement, 87, 138.
Maurin, M., Mersali, N. F., & Raoult, D. (2000). Bactericidal activities of antibiotics against intracellular Francisella tularensis. Antimicrobial agents and chemotherapy, 44(12), 3428-3431.
Luna, V. A., King, D. S., Gulledge, J., Cannons, A. C., Amuso, P. T., & Cattani, J. (2007). Susceptibility of Bacillus anthracis, Bacillus cereus, Bacillus mycoides, Bacillus pseudomycoides and Bacillus

(56) References Cited

OTHER PUBLICATIONS thuringiensis to 24 antimicrobials using Sensititre® automated microbroth dilution and Etest® agar gradient diffusion methods. Journal of antimicrobial chemotherapy, 60(3), 555-567.
Barthel, D., Schlitzer, M., & Pradel, G. (2008). Telithromycin and quinupristin-dalfopristin induce delayed death in Plasmodium falciparum. Antimicrobial agents and chemotherapy, 52(2), 774-777.
Still, J. G., et al. "Single Oral Dose Pharmacokinetics and Safety of CEM-101 in Healthy Subjects." 46th Annual Meeting. Idsa, 2008.
Lee, Joo Hyun, and Myung Gull Lee. "Dose-dependent pharmacokinetics of telithromycin after intravenous and oral administration to rats: contribution of intestinal first-pass effect to low bioavailability." J. Pharm. Pharm. Sci 10 (2007): 37-50.
Chen, M., Muri, E. M., Jacob, T. M., & Williamson, J. S. (2003). Synthesis and bioactivity of erythromycin derivatives. Medicinal chemistry research, 12(3), 111-129.
Kerdesky, F. A., Premchandran, R., Wayne, G. S., Chang, S. J., Pease, J. P., Bhagavatula, L., . . . & King, S. A. (2002). Synthesis of 2'-O-Benzoyl-3-keto-6-O propargyl-11, 12-carbamoyl Erythromycin A. Organic process research & development, 6(6), 869-875.
Zhu, Z. J., Krasnykh, O., Pan, D., Petukhova, V., Yu, G., Liu, Y., . . . & Franzblau, S. G. (2008). Structure-activity relationships of macrolides against Mycobacterium tuberculosis. Tuberculosis, 88, S49-S63.
Putnam S. D. et al, Antimicrobial Characterization of Solithromycin (Cem-101), A Novel Fluroroketolide: Activity Against Staphlococci and Enterococci. International Journal of Antimicrobial Agents, vol. 37, No. 1, 2011, pp. 39-45.
Written Opinion, Singapore Application No. 11201405895U: Intellectual Property Office of Singapore; Mar. 31, 2015, 6 pages.
Database WPI Week 200822 Thomson Scientific, London, GB; AN 2008-D02982.
Zimmermann, Torsten, et al. "Comparative tolerability of intravenous azithromycin, clarithromycin and erythromycin in healthy volunteers." Clinical Drug Investigation 21.8 (2001): 527-536.
Luke, D. R., and G. Foulds. "Toleration of intravenous azithromycin." The Annals of pharmacotherapy 31.9 (1997): abstract only.
Cannon, John B., N. Adeyinka Williams, and Karen J. Papp. "Reduction of pain on intravenous infusion with bile salt formulations for a macrolide antibiotic." International journal of pharmaceutics 114.1 (1995): abstract only.
Lu, Yan, YanJiao Wang, and Xing Tang. "Formulation and thermal sterile stability of a less painful intravenous clarithromycin emulsion containing vitamin E." International journal of pharmaceutics 346.1 (2008): abstract only.
Llano-Sotelo, B., D. Klepacki, and A. S. Mankin. 2008. Binding and action of CEM-10, a new macrolide/ketolide in development for treating infections with macrolide-resistant and macrolide-susceptible bacteria. 48th Annu. Intersci. Conf. Antimicrob. Agents Chemother./46th Infect. Dis. Soc. Am. Ann. Meet., abstr. F1-3983.
International Search Report for PCT/US2015/015353, dated May 14, 2015, (8 pages).
Ferris, C. F., Lu, S. F., Messenger, T., Guillon, C. D., Heindel, N., Miller, M., . . . & Simon, N. G. (2006). Orally active vasopressin V1a receptor antagonist, SRX251, selectively blocks aggressive behavior. Pharmacology Biochemistry and Behavior, 83(2), 169-174.
Amsden, G. W. "Anti-inflammatory effects of macrolides an underappreciated benefit in the treatment of community-acquired respiratory tract infections and chronic inflammatory pulmonary conditions?." Journal of Antimicrobial Chemotherapy 55.1 (2005): 10-21.
de Jong, J. T., et al. "[Large-scale, acute, bacterial gastroenteritis caused by the enterotoxin of Staphylococcus aureus after a barbecue]." Nederlands tijdschrift voor geneeskunde 148.43 (2004): 2136-2140.
Raj, Pushker. "Pathogenesis and laboratory diagnosis of Escherichia coli associated enteritis." Clinical microbiology Newsletter 15.12 (1993): 89-93.
Ikeue, T., et al. "[Pneumonia caused by Nocardia nova]." Nihon Kokyuki Gakkai zasshi= the journal of the Japanese Respiratory Society 39.7 (2001): 492-497.
Thakkar, Shyam, and Radheshyam Agrawal. "A case of Staphylococcus aureus enterocolitis: a rare entity." Gastroenterology & hepatology 6.2 (2010): 115-117.
Wain, Harry, and Paul A. Blackstone. "Staphylococcal Gastroenteritis." The American journal of digestive diseases 1.10 (1956): 424.
Boyce, Thomas G., "Staphylococcal Food Poisoning," Merck Manuals (2015) 2 pages.
Lv Yang et al., "Polymorphic Drugs." Oct. 31, 2009, pp. 110-111.
Le Loir, Yves, Florence Baron, and Michel Gautier. "Staphylococcus aureus and food poisoning." Genet Mol Res 2.1 (2003): 63-76.
Brittain HG editor "Polymorphism in pharmaceutical solids", Chapter 1, pp. 1- 10 (Grant DJW) and Chapter 5, pp. 183-226 (1999).
Graeme, A. O'May, Nigel Reynolds, and George T. Macfarlane. "Effect of pH on an in vitro model of gastric microbiota in enteral nutrition patients." Applied and environmental microbiology 71.8 (2005): 4777-4783.
Cotter, Paul D., and Colin Hill. "Surviving the acid test: responses of gram-positive bacteria to low pH." Microbiology and Molecular Biology Reviews 67.3 (2003): 429-453.
Wain, Harry, and Paul A. Blackstone. "Staphylococcal Gastroenteritis." The American journal of digestive diseases 1.10 (1956): 424-429.
Lyczak, J. B., Cannon, C. L., & Pier, G. B. (2002). Lung infections associated with cystic fibrosis. Clinical microbiology reviews, 15(2), 194-222.
Denis, Alexis, et al. "Synthesis and antibacterial activity of HMR 3647 a new ketolide highly potent against erythromycin-resistant and susceptible pathogens." Bioorganic & medicinal chemistry letters 9.21 (1999): 3075-3080.
Bryskier, A. "Ketolides—telithromycin, an example of a new class of antibacterial agents." Clinical Microbiology and Infection 6.12 (2000): 661-669.
Morimoto, Shigeo, et al. "Chemical modification of erythromycins. I. Synthesis and antibacterial activity of 6-O-methylerythromycins A." The Journal of antibiotics 37.2 (1984): 187-189.
Hällgren, Anita, et al. "Antimicrobial susceptibility patterns of enterococci in intensive care units in Sweden evaluated by different MIC breakpoint systems." Journal of Antimicrobial Chemotherapy 48.1 (2001): 53-62.
Fernandes, P., et al. Intravenous Formulation of Solithromycin, a Painless Macrolide Antibiotic in a Rabbit Intravenous Injection Model, 2011, 5 pages.
Allen Loyd V Jr, Acidifying Agents, Featured Excipient. International Journal of Pharmaceutical Compounding, Dec. 31, 1999, vol. 3, No. 4, pp. 309 (abstract only).
Yatin R. G. et al., Excipients for Protein Drugs. Excipient Development for Pharmaceutical, Biotechnology, and Drug Delivery Systems, Jul. 28, 2006, pp. 299-300.
Fernandes, P., et al. "Solithromycin Macrolide Antibiotic." Drugs of the Future 36.10 (2011): 751-758.

\* cited by examiner

US 9,815,863 B2

HYDROGEN BOND FORMING FLUORO KETOLIDES FOR TREATING DISEASES

CROSS-REFERENCE TO RELATED APPLICATIONS

This application is a U.S. national application under 37 C.F.R. §371(b) of International Application Serial No. PCT/US2011/051064 filed Sep. 9, 2011, which claims the benefit under 35 U.S.C. §119(e) of U.S. provisional application 61/381,794, filed 10 Sep. 2010, each of which is are incorporated by reference herein.

TECHNICAL FIELD

The invention described herein pertains to a novel macrolide antibacterial agent of formula (I), as defined below, and pharmaceutically acceptable salts, solvates, and hydrates thereof. Inter alia, the new macrolide antibacterial agent is active against a number of bacterial species, including resistant species.

BACKGROUND AND SUMMARY OF THE INVENTION

Macrolide antibiotics, characterized by a large lactone ring to which are attached one or more deoxy sugars, usually cladinose and desosamine, are antimicrobial drugs that are active against aerobic and anaerobic gram positive cocci and are prescribed for the treatment of respiratory tract and soft tissue infections. The macrolides, which belong to the polyketide class of natural products, function by reversibly binding to the 23S rRNA component of the 50S subunit of the bacterial ribosome, blocking protein synthesis and preventing bacterial growth and reproduction. The macrolide antibiotics bind to the large ribosomal subunit and inhibit protein synthesis by blocking the path of the nascent peptide in the exit tunnel (Gaynor, M., and A. S. Mankin. 2003. Macrolide antibiotics: binding site, mechanism of action, resistance. Curr. Top. Med. Chem. 3:949-961). The chemical structure of the prototype macrolide erythromycin A is represented by a 14-atom lactone ring substituted with 3-O-cladinose and 5-O-desosamine sugar residues. Macrolides of the subsequent generations differ in the structures of the lactone, such as azithromycin, as well as the number, composition, and sites of attachment of the side chains (Franceschi, F., Z. Kanyo, E. C. Sherer, and J. Sutcliffe. 2004. Macrolide resistance from the ribosome perspective. Curr. Drug Targets Infect. Disord. 4:177-191; Sutcliffe, J. A. 2005. Improving on nature: antibiotics that target the ribosome. Curr. Opin. Microbiol. 8:534-542).

The binding site of macrolides in the ribosome includes the 23S rRNA residues A2058, A2059, A2062, A2503, G2505, and C2611 [or U2611] (using here and throughout the E. coli numbering, see Tu, D., G. Blaha, P. B. Moore, and T. A. Steitz. 2005. Structures of MLSBK antibiotics bound to mutated large ribosomal subunits provide a structural explanation for resistance. Cell 121:257-270). It is to be understood that the corresponding nucleic acid residues in ribosomes of other organisms are described herein by reference to the E. coli nucleic acids. One of the main mechanisms of resistance to macrolide antibiotics is based on dimethylation of A2058 by methyltransferase encoded in erm genes (Weisblum, B. 1995. Erythromycin resistance by ribosome modification. Antimicrob. Agents Chemother. 39:577-585). Erm-catalyzed dimethylation of A2058 leads to a steric clash with the drug and reduces affinity of erythromycin for the ribosome. Similar to several other antibiotic resistance genes, erm genes are often inducible by erythromycin and similar drugs. In an effort to combat resistance, a newer class of macrolides, known as ketolides, was developed (Bryskier, A. 2000. Ketolides-telithromycin, an example of a new class of antibacterial agents. Clin. Microbiol. Infect. 6:661-669). Ketolides show improved activity against strains with inducible erm genes and are believed to exhibit a tighter binding to the ribosome compared with macrolides of the previous generations (Poehlsgaard, J., and S. Douthwaite. 2003. Macrolide antibiotic interaction and resistance on the bacterial ribosome. Curr. Opin. Investig. Drugs 4:140-148; Poehlsgaard, J., P. Pfister, E. C. Bottger, and S. Douthwaite. 2005. Molecular mechanisms by which rRNA mutations confer resistance to clindamycin. Antimicrob. Agents Chemother. 49:1553-1555). In ketolides, the 3-O-cladinose is replaced by a keto function (hence the name of the class); a cyclic carbamate is fused at the C11-C12 position; and an extended side chain, such as an alkyl side chain bearing a an aryl or heteroaryl group, which may be substituted, is attached at the C11-N atom (11-N) of the carbamate, as in the ketolide telithromycin, or at another position of the lactone ring, such as the 6-O— position as in cethromycin. Early biochemical and genetic studies showed that the extended side chain of ketolides establishes important new interactions with the ribosome that might account for increased efficacy of these drugs. Specifically, chemical probing and resistance mutations pointed to interactions of the 11-N-side chain of telithromycin with the rRNA residues in the loop of helix 35 of the E. coli 23S rRNA and with U2609 (Garza-Ramos, G., L. Xiong, P. Zhong, and A. Mankin. 2002. Binding site of macrolide antibiotics on the ribosome: new resistance mutation identifies a specific interaction of ketolides with rRNA. J. Bacteriol. 183:6898-6907; Hansen, L. H., P. Mauvais, and S. Douthwaite. 1999. The macrolide-ketolide antibiotic binding site is formed by structures in domains II and V of 23S ribosomal RNA. Mol. Microbiol. 31:623-632; Xiong, L., S. Shah, P. Mauvais, and A. S. Mankin. 1999. A ketolide resistance mutation in domain II of 23S rRNA reveals proximity of hairpin 35 to the peptidyl transferase centre. Mol. Microbiol. 31:633-639 46). However, subsequent crystallographic studies of the first clinically approved ketolide telithromycin bound to the bacterial (*Deinococcus radiodurans*) or archaeal (*Haloarcula marismortui*) ribosome showed the placement of the 11N-side chain in a position that appeared incompatible with rRNA protections and mutations observed in the *E. coli* ribosome (Berisio, R., J. Harms, F. Schluenzen, R. Zarivach, H. A. Hansen, P. Fucini, and A. Yonath. 2003. Structural insight into the antibiotic action of telithromycin against resistant mutants. J. Bacteriol. 185:4276-4279; 41). Furthermore, orientation of the 11-N-side chain differed significantly between the reported *D. radiodurans* and *H. marismortui* structures, therefore leaving open the question of how telithromycin would bind to the ribosomes of bacteria targeted by ketolide antibiotics, including Gram positive pathogenic bacteria.

Although telithromycin, the first ketolide introduced into medical practice in 2001, showed excellent activity against many strains of Gram positive pathogens, the safety issues that became apparent upon the wider use of the drug have curbed its clinical use (reviewed in Rafie, S., C. MacDougall, and C. L. James. 2010. Cethromycin: a promising new ketolide antibiotic for respiratory infections. Pharmacotherapy 30:290-303). The adverse effects associated with telithromycin spurred a search for newer ketolides. One of the novel promising drugs of this class is the fluoroketolide CEM-101 disclosed in international patent application, publication number WO 2004/080391, and its counterpart publication US 2006/0100164, at Example 7 and identified as OP-1068. The structure of CEM-101 is similar to that of telithromycin except for the presence of a fluorine atom at C2 of the lactone and the differing aromatic groups on the 11-N side chain (which in CEM-101 is a 4-[4-(3-aminophenyl)[1,2,3]triazol-1-yl]butyl group). Additional fluoroketolides are reported in C.-H. Liang et al., Bioorg. Med. Chem. Lett. 15 (2005) 1307-1310.

In microbiological tests involving a number of clinical pathogens, CEM-101 is characterized by lower minimal inhibitory concentration (MIC) values compared with telithromycin and exhibits enhanced activity against resistant organisms, including telithromycin-intermediate and telithromycin-resistant organisms (McGhee, P., C. Clark, K. M. Kosowska-Shick, K. Nagai, B. Dewasse, L. Beachel, and P. C. Appelbaum. 2010. In vitro activity of CEM-101 against *Streptococcus pneumoniae* and *Streptococcus pyogenes* with defined macrolide resistance mechanisms. Antimicrob. Agents. Chemother. 54:230-238). Furthermore, in comparison with telithromycin and cladinose-containing macrolides CEM-101 shows significantly enhanced accumulation in the macrophages.

It has been discovered that upon analysis of the binding interactions of CEM-101 compared to telithromycin and other macrolides, ketolides may be designed with high activity against pathogenic bacteria and against resistant strains of bacteria, including strains resistant to other ketolides like telithromycin.

In one illustrative embodiment of the invention, compounds of formula (I)

A-L-Q (I)

are described herein, and pharmaceutically acceptable salts, hydrates, solvates, and prodrugs thereof, wherein:
A is a moiety capable of forming one or more of the hydrogen bond interactions with one or more of A752, G748, and G748;
L is a linking chain consisting of one or more divalent radicals selected from the group consisting of amino, O, and S, and alkylene, heteroalkylene, cycloalkylene, heterocycloalkylene, alkenylene, heteroalkenylene, cycloalkenylene, heterocycloalkenylene, arylene, and heteroarylene, each of which is optionally substituted, provided that L does not include an O-O or O—S; and
Q is a 3-keto- or 2-fluoro-3-keto macrolactone capable of binding in the major macrolide site in the upper part of a bacterial ribosomal exit tunnel.

In another embodiment, compounds of formula (I) are described where Q is of the formula

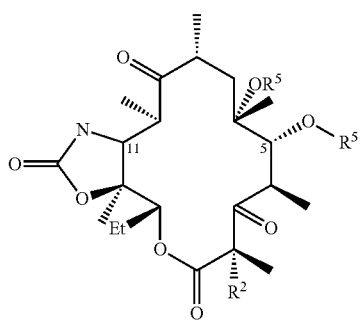

(Q)

in which L is bonded to the 11-N of Q;
$R^2$ is H or F;
$R^5$ is an aminosaccharide residue; and
$R^6$ is H or (1-6C)alkyl; and
wherein A-L- is other than 4-[4-(3-aminophenyl)[1,2,3]triazol-1-yl]butyl or 4-[4-(6-aminopyridin-2-yl)[1,2,3]triazol-1-yl]butyl bonded to the 11-N of Q.

In another embodiment, compounds of formula (I) are described herein, and pharmaceutically acceptable salts, hydrates, solvates, and prodrugs thereof, wherein (a) A is a moiety capable of forming one or more of the hydrogen bond interactions with one or more of O4' of A752 (as a donor), O6 of G748 (as a donor), and N1 of G748 (as an acceptor). In another embodiment, (b) the 3-keto group of Q is capable of forming a hydrogen bond interaction with U2609. In another embodiment, (c) the aminosaccharide of Q is capable of forming a hydrogen bond interaction with A2059. In another embodiment, (d) the aminosaccharide of Q is capable of forming a hydrogen bond interaction with G2505. In another embodiment, compounds of formula (I) are described herein, and pharmaceutically acceptable salts, hydrates, solvates, and prodrugs thereof, wherein the compound exhibits any combination of (a), (b), (c), and (d).

It is to be understood that the hydrogen bond forming capability of A may be determined using any conventional method. For example, hydrogen bond forming capability of A may be determined by computer modeling the compound in the *E. coli* 23S ribosomal site; or by co-crystallizing the compound in the *E. coli* 23S ribosomal site.

It is to be further understood that the hydrogen bond forming capability of the 3-keto group of Q may be determined using any conventional method. For example, in another embodiment, the compound protects U2609 from modification by CMCT, such as protecting against modification to a greater extent than does telithromycin, in RNA footprinting.

It is to be further understood that the hydrogen bond forming capability of the aminosaccharide of Q may be determined using any conventional method. For example, in another embodiment, the compound protects G2505 from modification by kethoxal, such as protecting against modification to a greater extent than does erythromycin, clarithromycin, azithromycin, and/or telithromycin, in RNA footprinting. In another embodiment, the compound blocks methylation of A2059 by DMS, such as blocking methylation to a greater extent than does erythromycin, clarithromycin, azithromycin, and/or telithromycin, in RNA footprinting.

In alternatives of each of the embodiments described herein, the bacteria may be a resistant strain. Illustrative resistant strains, include but are not limited to erythromycin resistant strains, clarithromycin resistant strains, azithromycin resistant strains, telithromycin resistant strains, mefA resistant strains, and ermB resistant strains.

DETAILED DESCRIPTION

Embodiments of the invention include those described by the following enumerated clauses:
1A. A compound of formula I,

A-L-Q (I)

or a pharmaceutically acceptable salt thereof,
wherein:
A is a hydrogen bond forming group;
L is a bivalent linking group comprising one or more units selected from the group consisting of optionally substituted methylene, O, S, optionally substituted NH, sulfonyl, vinylene, and cyclic units selected from the group consisting of divalent monocyclic and bicyclic carbocyclic and aromatic rings, and monocyclic and bicyclic heterocyclic and heteroaromatic rings, where the monocyclic and bicyclic heterocyclic and heteroaromatic rings contain 1 to 4 hetero atoms each independently selected from oxygen, sulfur and nitrogen, and where the cyclic units contain 5 to 10 ring atoms which are optionally substituted; providing that L does not include —O—O— or —O—S—;

Q is

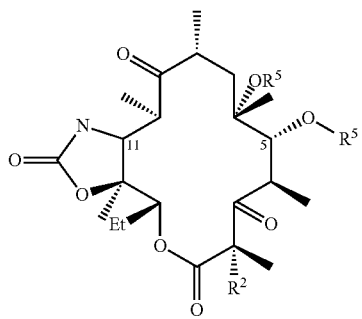

(Q)

in which L is bonded to the 11-N of Q;

$R^2$ is H or F;

$R^5$ is an aminosaccharide residue; and $R^6$ is H or (1-6C)alkyl; and where (a) A is capable of forming a hydrogen bond interaction in a bacterial ribosome selected from the group consisting of hydrogen bond donation to O4' of A752, hydrogen bond donation to 06 of G748, and hydrogen bond acceptance from N1 of G748; or (b) the 3-keto group of Q is capable of forming a hydrogen bond interaction with U2609; or (c) the aminosaccharide of Q is capable of forming a hydrogen bond interaction with A2059; or (d) the aminosaccharide of Q is capable of forming a hydrogen bond interaction with G2505; or any combination of (a), (b), (c), and (d); and wherein A-L- is other than 4-[4-(3-aminophenyl)[1,2,3]triazol-1-yl]butyl or 4-[4-(6-aminopyridin-2-yl)[1,2,3]triazol-1-yl]butyl.

1B. A compound of formula I,

A-L-Q   (I)

or a pharmaceutically acceptable salt thereof, wherein,

A. when the compound is modeled in the *E. coli* 23S ribosomal site, or

B. when the compound is co-crystallized in the *E. coli* 23S ribosomal site,

A is a moiety capable of forming one or more of the hydrogen bond interactions of the group consisting of hydrogen bond donation to O4' of A752, hydrogen bond donation to 06 of G748, and hydrogen acceptance from N1 of G748; or C. the compound in RNA footprinting of *S. aureus* N315 ribosomes protects U2609 from modification with CMCT to a greater extent than does telithromycin, or D. the compound in RNA footprinting of *S. aureus* N315 ribosomes blocks methylation of A2059 with DMS to a greater extent than does telithromycin, or E. the compound in RNA footprinting of *S. aureus* N315 ribosomes protects G2505 from modification with kethoxal to a greater extent than does telithromycin, or any combination of A, B, C, D and E;

L is a linking chain comprising one or more units selected from the group consisting of optionally substituted methylene, O, S, optionally substituted NH, vinylene, and a divalent monocyclic or bicyclic carbocyclic or aromatic or monocyclic or bicyclic heterocyclic or heteroaromatic ring containing 1 to 4 hetero atoms selected from O, S and N which ring contains 5 to 10 ring atoms and may bear one or more substituents, provided L does not include an —O—O— or —O—S— portion;

Q is

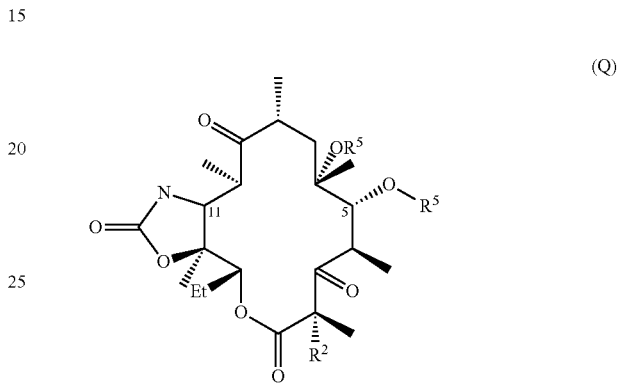

(Q)

in which L is bonded to the 11-N of Q;

$R^2$ is H or F;

$R^5$ is an aminosaccharide residue; and $R^6$ is H or (1-6C)alkyl; and wherein A-L- is other than 4-[4-(3-aminophenyl)[1,2,3]triazol-1-yl]butyl or 4-[4-(6-aminopyridin-2-yl)[1,2,3]triazol-1-yl]butyl bonded to the 11-N of Q.

2. The compound of clause 1A or 1B wherein A is capable of forming a hydrogen bond interaction selected from the group consisting of hydrogen bond donation to O4' of A752, hydrogen bond donation to 06 of G748, and hydrogen bond acceptance from N1 of G748.

3. The compound of clause 1A or 1B wherein A is capable of forming a hydrogen bond interaction selected from the group consisting of hydrogen bond donation to O4' of A752, and hydrogen bond donation to 06 of G748.

4. The compound of clause 1A or 1B wherein (a) A is capable of forming a hydrogen bond interaction selected from the group consisting of hydrogen bond donation to O4' of A752, hydrogen bond donation to 06 of G748, and hydrogen bond acceptance from N1 of G748; and (b) the 3-keto group of Q is capable of forming a hydrogen bond interaction with U2609; an (c) the aminosaccharide of Q is capable of forming a hydrogen bond interaction with A2059; and (d) the aminosaccharide of Q is capable of forming a hydrogen bond interaction with G2505.

5. The compound of clause 1A or 1B wherein the atom of A involved in hydrogen bond donation or acceptance is connected to 11-N of Q by a chain of at least about 9 atoms, where the chain may optionally be included in one or more cyclic groups.

6. The compound of clause 1A or 1B wherein the atom of A involved in hydrogen bond donation or acceptance is connected to 11-N of Q by a chain of at least about 10 atoms, where the chain may optionally be included in one or more cyclic groups.

7. The compound of clause 1A or 1B wherein the atom of A involved in hydrogen bond donation or acceptance is connected to 11-N of Q by a chain of about 10 or about 11 atoms, where the chain may optionally be included in one or more cyclic groups.

8. The compound of clause 1A or 1B wherein the atom of A involved in hydrogen bond donation or acceptance is connected to 11-N of Q by a chain of about 10 atoms, where the chain may optionally be included in one or more cyclic groups.

9. The compound or salt of any of the preceding clauses wherein the atom of A involved in hydrogen bond donation or acceptance is a nitrogen or an oxygen.

10. The compound or salt of clause 9 wherein A comprises a heterocyclic ring and the atom of A involved in hydrogen bond donation or acceptance is an atom of the heterocyclic ring.

11. The compound or salt of clause 10 wherein the heterocyclic ring is monocyclic or bicyclic heteroaromatic ring containing 1 to 4 hetero atoms selected from O, S and N which ring may bear one or more substituents.

12. The compound or salt of clause 9 wherein the atom of A involved in hydrogen bond donation or acceptance is part of an amino or a hydroxy group.

13. The compound or salt of any of the preceding clauses wherein the atom of A involved in hydrogen bond donation or acceptance is within 5 to 0.5 Å of at least one of O4' of A752, O6 of G748, and N1 of G748 of the model.

14. The compound or salt of any of the preceding clauses wherein $R^2$ is F.

15. The compound or salt of clause 14 wherein the 2-fluoro group is within 5 to 0.5 Å of the glycosidic bond (atom N1) of C2611 of the model.

16. The compound or salt of any of the preceding clauses wherein $R^5$ is desosaminyl.

17. The compound or salt of any of the preceding clauses wherein $R^6$ is methyl.

18. The compound or salt of any of the preceding clauses wherein $R^{11}$ is H.

19. The compound or salt of any of the preceding clauses wherein L is —$X_a$—$Y_b$—$Z_c$— in which X, Y and Z are divalent moieties;
each of a, b and c is independently 0 or 1, provided at least one of a, b and c is 1;
X is $CH_2R^aR^b$, O, S or $NR^c$;
Y is an monocyclic or bicyclic aromatic or a monocyclic or bicyclic heteroaromatic ring containing 1 to 4 hetero atoms selected from O, S and N which ring may bear one or more substituents;
Z is —$(CH_2)_m$— in which m is 1, 2, 3 or 4, one or more methylene units may bear one or two methyl groups, and a methylene unit may be replaced by O, S or $NR^d$; and
each of $R^a$, $R^b$, $R^c$ and $R^d$ is independently H or $CH_3$.

20. The compound or salt of any of the preceding clauses wherein A is indolyl other than 1-indolyl.

21. The compound or salt of clause 20 wherein A is 3-indolyl.

22. The compound or salt of any of the preceding clauses 1A-19 wherein A is 3-aminophenyl.

23. The compound or salt of any of the preceding clauses 1A-19 wherein A is 6-aminopyridin-2-yl.

24. The compound or salt of any of the preceding clauses 1A-19 wherein A is 3-hydroxyphenyl.

25. The compound or salt of any of the preceding clauses wherein a is 0.

26. The compound or salt of any of the preceding clauses wherein a is 1.

27. The compound or salt of any of the preceding clauses wherein X is $CH_2$.

28. The compound or salt of any of the preceding clauses wherein X is O.

29. The compound or salt of any of the preceding clauses wherein b is 1.

30. The compound or salt of any of the preceding clauses wherein Y is meta-phenylene.

31. The compound or salt of any of the preceding clauses wherein Y is a divalent 5-membered heteroaromatic residue in which the bonds are in a 1,3- (or equivalent) relationship.

32. The compound or salt of clause 31 wherein Y is [1,2,3]triazol-1,4-diyl, in either orientation.

33. The compound or salt of clause 32 wherein Y is [1,2,3]triazol-1,4-diyl, in which Z is bonded to the 1-position.

34. The compound or salt of any of the preceding clauses wherein c is 1.

35. The compound or salt of clause 34 wherein Z is —$(CH_2)_4$—, —$(CH_2)_3$—O—, —$(CH_2)_4$— —$(CH_2)_3$—NH—, —$(CH_2)_3$—, —$(CH_2)_2$—O—, —$(CH_2)_2$—NH—, or —$(CH_2)_2$—.

36. The compound or salt of clause 35 wherein Z is —$(CH_2)_4$— or —$(CH_2)_3$—.

37. The compound or salt of any of the preceding clauses wherein each of b and c is 1.

38. The compound or salt of clause 37 wherein a is 0.

39. The compound or salt of any of the preceding clauses wherein each of a, b and c is 1.

40. The compound or salt of any of the preceding clauses wherein A-X—Y— is 4-(indol-3-ylmethyl) [1,2,3]triazol-1-yl.

41. The compound or salt of any of the preceding clauses wherein A-L- is 4-[4-(indol-3-ylmethyl) [1,2,3]triazol-1-yl] butyl.

42. The compound or salt of any of the preceding clauses wherein the *E. coli* 23S ribosomal site is defined by the X-ray coordinates of the complex of CEM-101 with the *E. coli* 23S ribosome.

43. The compound of clause 1A or 1B wherein the compound is

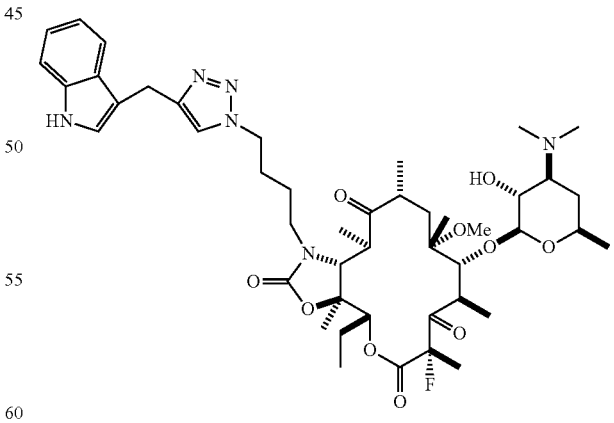

2-fluoro-5-O-desosaminyl-11-N-[4-[4-(indol-3-ylmethyl) [1,2,3]triazol-1-yl]butyl]-6-O-methyl-3-oxo-erythronolide A 11,12-cyclic carbamate, or a pharmaceutically acceptable salt thereof.

44. A pharmaceutical composition comprising an agent of formula (I), as described in any of the preceding clauses 1A-43 and further comprising at least one pharmaceutically acceptable carrier or excipient.

45. A method of treatment of a bacterial infection, a protozoal infection, or a disorder related to a bacterial infection or protozoal infection comprising the step of administering to a subject in need thereof a therapeutically effective amount of an agent of formula (I), as described in any of the preceding clauses 1A-43.

46. Use of an agent of formula (I), as described in any of the preceding clauses 1A-43 for the treatment of a bacterial infection, a protozoal infection, or a disorder related to a bacterial infection or protozoal infection.

47. Use of an agent of formula (I), as described in any of the preceding clauses 1A-43 for the manufacture of a medicament for the treatment of a bacterial infection, a protozoal infection, or a disorder related to a bacterial infection or protozoal infection.

48. The method or use of any of clauses 45-47 wherein the subject is a mammal, a fish, a bird or a reptile.

49. The method or use of clause 48 wherein the subject is a mammal.

50. The method or use of clause 49 wherein the subject is a human.

In another embodiment, compounds of formula (I) are described herein, and pharmaceutically acceptable salts, hydrates, solvates, and prodrugs thereof, wherein Q is a macrolactone where the lactone ring forms positive hydrophobic interactions with the walls of the tunnel.

In another embodiment, compounds of formula (I) are described herein, and pharmaceutically acceptable salts, hydrates, solvates, and prodrugs thereof, wherein Q is a macrolactone substituted with a desosamine, where the desosamine sugar projects toward the peptidyl transferase center and interacts with the A2058/A2509 cleft.

In another embodiment, compounds of formula (I) are described herein, and pharmaceutically acceptable salts, hydrates, solvates, and prodrugs thereof, wherein A-L- is arylalkyl, and the arylalkyl arm is oriented down the tunnel and makes contact with a base pair formed by A752 and U2609 of the 23S rRNA.

In another embodiment, compounds of formula (I) are described herein, and pharmaceutically acceptable salts, hydrates, solvates, and prodrugs thereof, wherein A-L has a low atomic displacement parameter (ADP).

In another embodiment, compounds of formula (I) are described herein, and pharmaceutically acceptable salts, hydrates, solvates, and prodrugs thereof, wherein Q is a macrolactone that includes a fluoro group capable of a positive interaction with the glycosidic bond (atom N1) of C2611. In another embodiment, compounds of formula (I) are described herein, and pharmaceutically acceptable salts, hydrates, solvates, and prodrugs thereof, wherein Q is a macrolactone that includes a fluoro group capable of a positive interaction with the glycosidic bond (atom N1) of C2611 of a ribosome present in a resistant bacteria, such as a ribosome monomethylated or dimethylated at A2058 and/or A2059.

In another embodiment, the foregoing positive interactions are positive interactions with a ribosome present in a resistant bacteria, such as a ribosome monomethylated or dimethylated at A2058 and/or A2059.

In another embodiment, compounds of formula (I) are described herein, and pharmaceutically acceptable salts, hydrates, solvates, and prodrugs thereof, wherein Q is a macrolactone substituted with a desosamine, where the desosamine protects A2058 and A2059 in domain V of 23S rRNA from modification with DMS. In another embodiment, compounds of formula (I) are described herein, and pharmaceutically acceptable salts, hydrates, solvates, and prodrugs thereof, wherein Q is a macrolactone substituted with a desosamine, where the desosamine protects A752 from DMS modification.

In another embodiment, compounds of formula (I) are described herein, and pharmaceutically acceptable salts, hydrates, solvates, and prodrugs thereof, wherein Q is a macrolactone substituted with a desosamine, where the desosamine protects A2059 in domain V of 23S rRNA in an erm resistant and/or erm modified bacteria from modification with DMS. In another embodiment, compounds of formula (I) are described herein, and pharmaceutically acceptable salts, hydrates, solvates, and prodrugs thereof, wherein Q is a macrolactone substituted with a desosamine, where the desosamine substantially protects A2059 in domain V of 23S rRNA in an erm resistant and/or erm modified bacteria from modification with DMS.

In another embodiment, compounds of formula (I) are described herein, and pharmaceutically acceptable salts, hydrates, solvates, and prodrugs thereof, wherein Q is a macrolactone substituted with a desosamine, where the desosamine protects G2505 from kethoxal modification. In another embodiment, compounds of formula (I) are described herein, and pharmaceutically acceptable salts, hydrates, solvates, and prodrugs thereof, wherein Q is a macrolactone substituted with a desosamine, where the desosamine substantially protects G2505 from kethoxal modification. In another embodiment, compounds of formula (I) are described herein, and pharmaceutically acceptable salts, hydrates, solvates, and prodrugs thereof, wherein Q is a macrolactone substituted with a desosamine, where the desosamine protects U2609 from modification with CMCT. In another embodiment, compounds of formula (I) are described herein, and pharmaceutically acceptable salts, hydrates, solvates, and prodrugs thereof, wherein Q is a macrolactone substituted with a desosamine, where the desosamine substantially protects U2609 from modification with CMCT.

It is to be understood that the compounds described herein may have one or more of the positive interactions and/or protections described in the foregoing embodiments, and that the corresponding embodiments that have any and all combinations of the foregoing positive interactions are explicitly described herein.

In each of the foregoing embodiments referring to positive interactions with and/or protections of ribosomal functional groups, it is to be understood that compounds are also described herein that have the corresponding and/or parallel positive interactions with and/or protections of other bacterial ribosomal functional groups, such as the corresponding functional groups in pathogenic bacteria, including but not limited to *S. aureus, S. pyogenes, S. penuomiae*, and the like, as well as resistant pathogenic bacterial strains, including but not limited to telithromycin resistant *S. aureus*, MRSA, and the like. Without being bound by theory, it is believed herein that methods for determining the capability of the compounds described herein to have positive interactions with and/or protections of ribosomal functional groups of *E. coli* as described herein, including computational methods, computer modeling, computational docking, energy minimization, X-ray crystallography, atomic displacement parameter (ADP) refinement, RNA footprinting, RNA binding assessments, and the like, may be predictive of the same, similar, equivalent, and/or corresponding interactions with pathogenic bacteria, including but not limited to *S. aureus, S. pyogenes, S. penuomiae*, and the like, as well as resistant pathogenic bacterial strains, including but not limited to telithromycin resistant *S. aureus*, MRSA, and the like.

As used herein, positive interactions are interactions that are lower energy states for the compound and/or the ribosome. Illustratively, positive interactions are those that are not sterically crowded, such as interactions that are at least about 0.5 Å or at least about 1 Å separated in space. Illustratively, positive interactions are those that are close enough to provide an energetic benefit, such as interactions that are about 5 Å or less, about 4.5 Å or less, about 4 Å or less, about 3.5 Å or less, about 3 Å or less, about 2.5 Å or less, about 1.5 Å or less, or about 1 Å or less, while at the same time at least about 0.5 Å separated in space.

In another embodiment, compounds of formula (I) are described herein, and pharmaceutically acceptable salts, hydrates, solvates, and prodrugs thereof, wherein in competition binding experiments, the compounds are capable of displacing erythromycin bound to a ribosome. In another embodiment, compounds of formula (I) are described herein, and pharmaceutically acceptable salts, hydrates, solvates, and prodrugs thereof, wherein in competition binding experiments, the compounds are capable of displacing telithromycin bound to a ribosome. Illustratively, the $IC_{50}$ of such displacement is about 1 µM or less, about 500 nM or less, about 250 nM or less, about 200 nM or less, about 150 nM or less, or about 100 nM or less.

It is to be understood that CEM-101 is not included in the invention described herein. It is also to be understood that telithromycin is not included in the invention described herein because it does not form a hydrogen bond with any of A752, G748, or G748.

In another embodiment, compositions comprising a therapeutically effective amount of one or more of compounds described herein are described. The compositions optionally include one or more diluents, excipients, or carriers, and combinations thereof.

In another embodiment, methods for treating a patient with a bacterial infection are described herein. The methods include the step of administering a therapeutically effective amount of one or more compounds and/or one or more compositions described herein to the patient.

In another embodiment, uses of one or more compounds and/or one or more compositions described herein in the manufacture of a medicament for treating a patient with a bacterial infection are described herein.

As used herein, when the compound is modeled in the *E. coli* 23S ribosomal site, it means that the compounds are characterized by docking into a calculated structure/conformation of an *E. coli* 23S bacterial ribosome, or a structure of the bacterial ribosome obtained from an X-ray crystal determination. Illustrative X-ray crystal determinations include those from studies of the binding of telithromycin (Berisio, R., J. Harms, F. Schluenzen, R. Zarivach, H. A. Hansen, P. Fucini, and A. Yonath. 2003. Structural insight into the antibiotic action of telithromycin against resistant mutants. J. Bacteriol. 185:4276-4279; Tu, D., G. Blaha, P. B. Moore, and T. A. Steitz. 2005. Structures of MLSBK antibiotics bound to mutated large ribosomal subunits provide a structural explanation for resistance. Cell 121:257-270), and particularly the determination wherein the *E. coli* 23S ribosomal site is defined by the X-ray coordinates of the complex of CEM-101 with the *E. coli* 23S ribosome described herein.

As used herein, docking refers to positioning the compound at/in the 23S ribosome, and may optionally include minimization calculations, such that once positioned there are no negative interactions which preclude docking. In addition to the placement and configuration of the lactone ring and the 5-0 sugar, the side chain may be capable of a stacking interaction with the A753/U2609 base pair and the 2-fluoro group, if present, is capable of an interaction with C2610 or C2611. For a compound of the invention, when the molecule is docked in the 23S ribosome, the moiety A is capable of forming one or more of the hydrogen bond interactions of the group consisting of hydrogen bond donation to O4' of A752, hydrogen bond donation to 06 of G748, and hydrogen acceptance from N1 of G748.

In embodiments described herein where A in the compounds is capable of forming one or more of the hydrogen bond interactions with one or more of A752, G748, and G748, and Q is a macrolactone substituted with a desosamine, where the desosamine sugar projects toward the peptidyl transferase center and interacts with the A2058/A2509 cleft, the compounds may be characterized by a calculated energy minima corresponding to a conformation where both A and the desosamine are positioned for each of the positive interactions, respectively.

In embodiments described herein where A in the compounds is capable of forming one or more of the hydrogen bond interactions with one or more of A752, G748, and G748, and Q is macrolactone that includes a fluoro group capable of a positive interaction with the glycosidic bond (atom N1) of C2611, the compounds may be characterized by a calculated energy minima corresponding to a conformation where both A and the fluoro group are positioned for each of the positive interactions, respectively.

In embodiments described herein where A in the compounds is capable of forming one or more of the hydrogen bond interactions with one or more of A752, G748, and G748, and Q is macrolactone that includes a fluoro group capable of a positive interaction with the glycosidic bond (atom N1) of C2611, and Q is a macrolactone substituted with a desosamine, where the desosamine sugar projects toward the peptidyl transferase center and interacts with the A2058/A2509 cleft, the compounds may be characterized by a calculated energy minima corresponding to a conformation where A, the fluoro group, and the desosamine are positioned for each of the positive interactions, respectively.

In variations of the foregoing embodiments the group A-L- is arylalkyl, and the arylalkyl arm is oriented down the tunnel and makes contact with a base pair formed by A752 and U2609 of the 23S rRNA, the compounds may be characterized by a calculated energy minimum corresponding to a conformation where A-L- is also positioned for the positive interaction.

It is to be understood that the calculated conformations may be obtained from any conventional software program. It is further to be understood that additional conformations may be calculated for the compounds when the initial conformations do not include a distance between a particular hydrogen-bonding group or the fluoro group and each required binding site of about 5 to 0.5 Å. Accordingly, those compounds that have additional conformations are to be understood to be included in the invention described herein. Illustrative calculations may be in the gas phase, ab initio, quasi solution sphere, and the like. It is appreciated that such calculations may be based on averages, or weighted averages.

In another embodiment, the compounds are characterized by high potency against pathogenic cells, such as bacteria. In another embodiment, the compounds are characterized by high potency against bacteria that are resistant to one or more other compounds. Illustrative resistant bacteria include, but are not limited to mefA resistant *S. pneumo*, ennB resistant *S. pneumo*, and the like.

In one embodiment of A, A is a phenyl, indenyl, naphthyl, furanyl, thiophenyl, pyrrolyl, oxadiazolyl, thiadiazolyl, imidazolyl, pyrazolyl, 1,2,4-oxadiazolyl, 1,2,4-thiadiazolyl, 1,3,4-oxadiazolyl; 1,3,4-thiadiazolyl, 1,2,3-triazolyl, 1,2,4-triazolyl, tetrazolyl, pyridinyl, pyridazinyl, pyrimidinyl, pyrazinyl, benzofuranyl, benzothiophenyl, indolyl, indazolyl, benzisoxazolyl, benzisothiazolyl, benzimidazolyl; benzoxazolyl; benzisothiazolyl, quinolinyl, isoquinolinyl or quinazolinyl, any of which may bear one or more hydroxy, amino, hydroxymethyl, aminomethyl, fluoro, chloro or methyl substituents.

In one embodiment for L, an optionally substituted methylene may bear one or two methyl groups; an optionally substituted NH may bear a methyl group; a divalent monocyclic or bicyclic carbocyclic or aromatic or monocyclic or bicyclic heterocyclic or heteroaromatic ring may be a cyclopropanediyl, cyclopentanediyl, cyclohexanediyl, cycloheptanediyl, phenylene, indanediyl, indenediyl, naphthalenediyl, tetrahydronaphthalenediyl, tetrahydrofurandiyl, pyrrolidinediyl, piperidinediyl, furandiyl, thiophenediyl, pyrrolediyl, oxazolediyl, thiazolediyl, imidazolediyl, pyrazolediyl, 1,2,4-oxadiazolediyl, 1,2,4-thiadiazolediyl, 1,3,4-oxadiazolediyl; 1,3,4-thiadiazolediyl, 1,2,3-triazolediyl, 1,2,4-triazolediyl, tetrazolediyl, pyridinediyl, pyridazinediyl, pyrimidinediyl, pyrazinediyl, benzofurandiyl, benzothiophenediyl, indolediyl, indazolediyl, benzisoxazolediyl, benzisothiazolediyl, benzimidazolediyl; benzoxazolediyl; benzisothiazolediyl, quinolinediyl, isoquinolinediyl or quinazolinediyl; and a ring may bear one or more hydroxy, fluoro, chloro or methyl substituents.

In one embodiment of Y, a divalent monocyclic or bicyclic aromatic or monocyclic or bicyclic heteroaromatic ring may be a phenylene, indanediyl, indenediyl, naphthalenediyl, tetrahydronaphthalenediyl, furandiyl, thiophenediyl, pyrrolediyl, oxazolediyl, thiazolediyl, imidazolediyl, pyrazolediyl, 1,2,4-oxadiazolediyl, 1,2,4-thiadiazolediyl, 1,3,4-oxadiazolediyl, 1,3,4-thiadiazolediyl, 1,2,3-triazolediyl, 1,2,4-triazolediyl, tetrazolediyl, pyridinedyl, pyridazinediyl, pyrimidinediyl, pyrazinediyl, benzofurandiyl, benzothiophenediyl, indolediyl, indazolediyl, benzisoxazolediyl, benzisothiazolediyl, benzimidazolediyl; benzoxazolediyl; benzisothiazolediyl, quinolinediyl, isoquinolinediyl or quinazolinediyl; and a ring may bear one or more hydroxy, fluoro, chloro or methyl substituents.

In one embodiment, A-X—Y— is selected from the following group of radicals, where Z is covalently connected at (*):

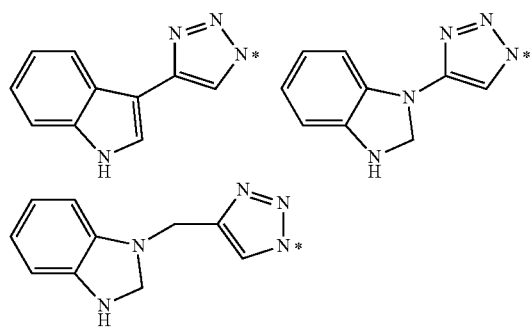

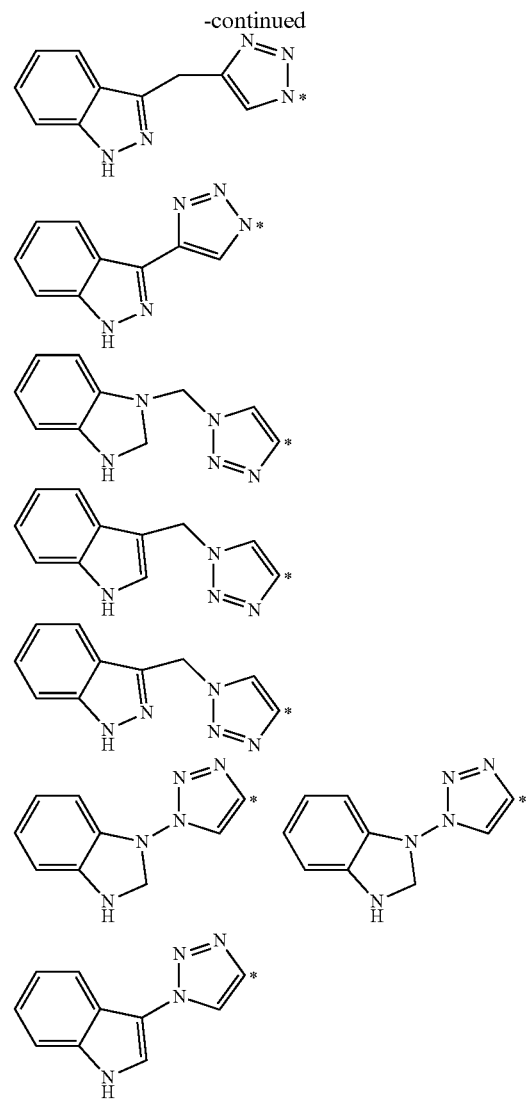

In one embodiment (1-6C)alkyl is methyl, ethyl, propyl, butyl, pentyl or hexyl, any of which may be branched. In another embodiment (1-6C)alkyl is methyl.

As another embodiment of the invention, there is provided a pharmaceutical composition comprising an agent of formula (I), as described in any of the descriptions herein and further comprising at least one pharmaceutically acceptable carrier or excipient.

Illustratively, compositions may include one or more carriers, diluents, and/or excipients. The compounds described herein, or compositions containing them, may be formulated in any conventional dosage forms appropriate for the methods described herein, and include one or more carriers, diluents, and/or excipients therefor. Such formulation compositions may be administered by a wide variety of conventional routes for the methods described herein, and in a wide variety of dosage formats, utilizing known procedures. Capsules and tablets are embodiments commonly used for oral administration of antibiotics. See generally, Remington: The Science and Practice of Pharmacy, (21st ed., 2005).

As another embodiment of the invention, there is provided a method of treatment of a bacterial infection, a protozoal infection, or a disorder related to a bacterial infection or protozoal infection comprising the step of administering to a subject in need thereof a therapeutically effective amount of an agent of formula (I), as described herein. Illustrative dosing schedules include administration of a loading dose on day 1 of 800 mg, followed by a dose of 400 mg/day on each of days 2-5, or, alternatively a loading dose on day 1 of 400 mg, followed by a dose of 200 mg/day on each of days 2-5.

As another embodiment of the invention, there is provided a use of an agent of formula (I), as described herein, for the treatment of a bacterial infection, a protozoal infection, or a disorder related to a bacterial infection or protozoal infection.

As another embodiment of the invention, there is provided a use of an agent of formula (I), as described herein, for the manufacture of a medicament for the treatment of a bacterial infection, a protozoal infection, or a disorder related to a bacterial infection or protozoal infection.

As a further embodiment, method or use described above is one wherein the subject is a mammal, a fish, a bird or a reptile. As another embodiment, there is provided a method or use wherein the subject is a mammal. As another embodiment, there is provided a method or use wherein the subject is a human.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill It is to be understood that compounds described herein in each embodiment are other than compounds wherein A-L- is: 4-[4-(3-aminophenyl)-[1,2,3]triazol-1-yl]butyl, 4-[4-(4-pentylphenyl)-[1,2,3]triazol-1-yl]butyl, 4-[4-(2-pyridinyl)-[1,2,3]triazol-1-yl]butyl, 4-[4-(6-aminopyridin-2-yl)-[1,2,3]triazol-1-yl]butyl, 4-[4-(3-aminophenylmethyl)-[1,2,3]triazol-1-yl]butyl, 4-[4-(2-pyridinylmethyl)-[1,2,3]triazol-1-yl]butyl, 4-[4-(6-aminopyridin-2-ylmethyl)-[1,2,3]triazol-1-yl]butyl, 4-[4-(2-pyridinylmethyl)-[1,2,3]triazol-1-yl]butyl, 4-[4-(benzimidazole-1-ylmethyl)-[1,2,3]triazol-1-yl]butyl, 4-[4-(7-azabenzimidazole-1-ylmethyl)-[1,2,3]triazol-1-yl]butyl, 4-[4-(2,6-dichloro-phenoxymethyl)-[1,2,3]triazol-1-yl]butyl, 4-[3-(2-pyridinylmethyl)-pyrazol-1-yl]butyl, 4-[3-(3-pyridinylmethyl)-pyrazol-1-yl]butyl, 4-[4-(3-aminophenyl)-imidazol-1-yl]butyl, 4-[4-(3-pyridinyl)-imidazol-1-yl]butyl, 4-[4-(3-indolyl)-imidazol-1-yl]butyl, 4-[4-(2-aminopyrimidin-5-yl)-imidazol-1-yl]butyl, 4-[4-(2-furanylcarbonylamino)-imidazol-1-yl]butyl, 4-(7-azabenzimidazole-1-yl)butyl, 4-azidobutyl, 3-(2-phenylimidazol-1-yl)propyl-amino, 3-[4-allylimidazol-1-yl]propylamino, 3-[4-(4,5-diacetoxy)imidazol-1-yl]propylamino, 3-[4-[2-(acetylamino)ethyl]-imidazol-1-yl]propylamino, 3-(5-phenyltetrazol-2-yl)propylamino, 3-[5-(2-chorophenyl)tetrazol-2-yl]propylamino, 3-[5-(4-chorophenyl)tetrazol-2-yl]propylamino, 3-(4-quinolinyl)propylamino, 3-(6-aminopurin-9-yl)propylamino, (R)-1-(2-benzimidazole-carbonyl)pyrrolidin-2-ylmethyl, (R)-1-(2-pyrrolo[2,3-a]pyridinecarbonyl)pyrrolidin-2-ylmethyl, (R)-1-(1-isoquinolinecarbonyl)pyrrolidin-2-ylmethyl, (R)-1-[1-(8-azaisoquinoline)carbonyl]-pyrrolidin-2-ylmethyl, 1-(8-azaquinolin-4-ylmethyl)azetidin-4-yl, 1-(3-hydroxy-5-azaquinolin-4-ylmethyl)azetidin-4-yl, (R)-1-[1-(8-azaquinolin-4-yl)ethyl]azetidin-4-yl, 1-(3-cyano-4-ethoxyphenylsulfonyl)azetidin-4-yl, 1-(8-quinoxolinesulfonyl)azetidin-4-yl, (R)-2-amino-1-(hydroxymethyl)ethyl, (R)-2-benzylamino-1-(hydroxymethyl)ethyl, quinoxolin-6-ylmethyl-aminocarbonylaminomethyl, and quinoxolin-6-ylmethyloxycarbonylaminomethyl. Accordingly, the foregoing compounds do not form part of the invention described herein.

Characterization of the mode of action and site of binding of CEM-101 was carried out as follows:

Materials and Methods

Example

Antibiotics, ribosomes, and reagents. CEM-101, CEM-103, telithromycin, and [$^{14}$C]CEM-101 (53 mCi/mmol), were synthesized by Moravek Biochemicals, Inc. Erythromycin and azithromycin were obtained from Sigma. [$^{14}$C] Erythromycin (48.8 mCi/mmol) was obtained from PerkinElmer.

Antibiotics were dissolved in 100% ethanol at a concentration of 10 mM, and serial dilutions were made in water to obtain the needed concentrations for competition binding studies and cell-free transcription-translation assays. The antibiotics were diluted in ethanol for ribosome probing experiments.

Ribosomes were prepared from *E. coli*, strain MRE 600, *S. aureus* strain ATCC 29212, or *S. aureus* strain N315 by standard protocols (Spedding™, G. 1990. Isolation and analysis of ribosomes from prokaryotes, eukaryotes, and organelles, p. 1-29. In G. Spedding (ed.), Ribosomes and protein synthesis, a practical approach. Oxford University Press, Oxford, United Kingdom; Adams, P. D., P. V. Afonine, G. Bunkoczi, V. B. Chen, I. W. Davis, N. Echols, J. J. Headd, L. W. Hung, G. J. Kapral, R. W. Grosse-Kunstleve, A. J. McCoy, N. W. Moriarty, R. Oeffner, R. J. Read, D. C. Richardson, J. S. Richardson, T. C. Terwilliger, and P. H. Zwart. 2010. PHENIX: a comprehensive Python-based system for macromolecular structure solution. Acta Crystallogr. D. Biol. Crystallogr. 66:213-221).

Most of the chemicals were obtained from Fisher Scientific or Sigma.

Example

Competition binding studies. Binding of erythromycin to *E. coli* and *S. aureus* ribosomes and competition experiments were done by size-exclusion chromatography using Bio-Gel P30 spin columns as described in Xiong, L., Y. Korkhin, and A. S. Mankin. 2005. Binding site of the bridged macrolides in the *Escherichia coli* ribosome. Antimicrob. Agents Chemother. 49:281-288.

Direct antibiotic binding experiments were done by incubating ribosomes at a 100 nM concentration with varying concentrations of radiolabeled drug in a total volume of 160 µL in buffer A (20 mM Tris-HCl [pH 7.5], 10 mM $MgCl_2$, 150 mM $NH_4Cl$, 6 mM 2-mercaptoethanol) at 37° C. for 15 min, then at 20° C. for 10 min. The reactions were loaded onto the spin columns and centrifuged in a swinging-bucket microcentrifuge rotor for 1 min at 1,000 g at room temperature. The flow-through solution was collected; 130 µL was mixed with 5 mL of the scintillation cocktail. Radioactivity was measured in a scintillation counter and used to calculate the amount of the radiolabeled drug bound to ribosomes.

For competition binding experiments, ribosomes (100 nM) were preincubated with 100 nM [$^{14}C$]erythromycin (48.8 mCi/mmol; PerkinElmer) in 160 µL of buffer A at 37° C. for 15 min, then at 20° C. for 10 min. Competing antibiotics were added at varying concentrations, and the binding mixture was incubated at 20° C. for 100 min. The reactions were loaded onto the spin columns and the amount of ribosome-associated radioactivity was measured as described above. Binding data were analyzed using Prism software (GraphPad). Cell free transcription-translation assays.

The *E. coli* transcription-translation (TnT) S30 extract system for circular DNA (Promega, Cat. No. L1020) was used to evaluate the effect of antibiotics on bacterial protein synthesis. Experiments were carried out in 96-well conical bottom plates in a final volume of 10 µL. S30 extract (3 µL) was dispensed into wells of the plate, combined with 1 µL of water or antibiotic solution, and preincubated at 25° C. for 5 min. The reactions were initiated by adding 6 µL of translation mix containing 1 µL of pBESTluc™ DNA (0.7 µg), 1 µL of 1 mM amino acid mixture, and 4 µL of S30 premix. Reactions were incubated at 20° C. for 40 min and then placed on ice. In another 96-well plate, 150 µL of Bright-Glo dilution reagent (Promega, Cat. No. E266A) was dispensed and mixed with 1.5 µL of the translation reactions; 30 µL of the resulting solution was mixed with 30 µL of Bright-Glo luciferase assay reagent (Promega, Cat. No. E2610) in a 96-well white-wall plate (PerkinElmer, Cat. No. 6005290). Luminescence was measured on a TopCount Scintillation and Luminescence Counter (PerkinElmer).

The rabbit reticulocyte cell-free translation system (Promega, Cat. No. L4540) was used to assay the effect of the drugs on activity of the eukaryotic ribosome. Experiments were carried out in 96-well conical bottom plates in a final volume of 10 µL. Rabbit reticulocyte lysate (7 µL) was mixed with 1 µL of water or antibiotics and preincubated at 25° C. for 5 min. Polyadenylated luciferase mRNA (Promega, Cat. No. L4561) was denatured before use by incubating the RNA at 65° C. for 3 min and then placed on ice. Translation mix (2 µL) was mixed with the rabbit reticulocyte lysate to start the reaction. The translation mix contained 0.3 µL of denatured luciferase mRNA (0.3 µg), 0.2 µL of 1 mM amino acid mixture, 0.2 µL of ribonuclease inhibitor (8U, Roche, Cat. No. 03 335 399001), 0.4 µL of 2.5 M potassium chloride, and 0.9 µL of water. Reactions were incubated at 30° C. for 30 min and then placed on ice. In another 96-well plate, 150 µL of Bright-Glo dilution reagent (Promega, Cat. No. E266A) was dispensed and mixed with 1.5 µL of the translation reactions; 30 µL of the resulting solution was mixed with 30 µL of Bright-Glo luciferase assay reagent (Promega, Cat. No. E2610) in a 96-well white-wall plate. Luminescence was measured on a TopCount Scintillation and Luminescence Counter (PerkinElmer).

Example

Ribosome chemical probing. rRNA probing was done following standard protocols (Merryman, C., and H. F. Noller. 1998. Footprinting and modification-interference analysis of binding sites on RNA, p. 237-253. In C. W. J. Smith (ed.), RNA:Protein Interactions, A Practical Approach. Oxford University Press, Oxford), with minor modifications. Briefly, 200 nM ribosomes were incubated with 100 µM antibiotic in 50 µL of buffer B (80 mM HEPES-KOH [pH 7.8], 20 mM $MgCl_2$, 100 mM $NH_4Cl$, 1.5 mM dithiothreitol) for 10 min at 37° C., followed by 10 min at 20° C. Modifying reagents (dimethyl sulfate [DMS], kethoxal, or 1-cyclohexyl-3-(2-morpholinoethyl)carbodiimide metho p-toluene sulfonate [CMCT]) were added and the modification reaction was carried out for 10 min at 37° C. After quenching the reaction and ethanol precipitation, rRNA was extracted and the distribution of modified nucleotides was assessed by primer extension.

Example

Crystallographic studies of CEM-101 complexed to the *E. coli* ribosome. Ribosomes were purified from MRE600 *E. coli* cells as described previously (Schuwirth™, B. S., M. A. Borovinskaya, C. W. Han, W. Zhang, A. Vila-Sanjurjo, J. M. Holton, and J. H. Cate. 2005. Structures of the bacterial ribosome at 3.5 Å resolution. Science 310: 827-834). Ribosome crystals were grown and handled as described (Zhang, W., J. A. Dunkle, and J. H. Cate. 2009. Structures of the ribosome in intermediate states of ratcheting. Science 325: 1014-1017), except that cryoprotection buffer was supplemented with 50 µM CEM-101. The crystals were soaked in cryoprotection buffer plus CEM-101 for 12 to 24 h, then flash frozen with liquid nitrogen. X-Ray diffraction data were collected at beamline 12.3.1 of the Advanced Light Source, Lawrence Berkeley National Laboratory, using 0.1°-0.3° oscillations at 100K and recorded on an ADSC Q315 detector. X-Ray diffraction data were reduced and scaled using HKL2000 (Otwinowski, Z., and M. W. 1997. Processing of X-ray Diffraction Data Collected in Oscillation Mode, p. 307-326. In C. W. J. Carter and S. R. M. (ed.), Methods Enzymol., vol. 276. Academic Press, New York). The coordinates reported in 3I1M, 3I1N, 3I1O, and 3I1P were refined against the reflection data using the PHENIX software suite (Adams, P. D., P. V. Afonine, G. Bunkoczi, V. B. Chen, I. W. Davis, N. Echols, J. J. Headd, L. W. Hung, G. J. Kapral, R. W. Grosse-Kunstleve, A. J. McCoy, N. W. Moriarty, R. Oeffner, R. J. Read, D. C. Richardson, J. S. Richardson, T. C. Terwilliger, and P. H. Zwart. 2010. PHENIX: a comprehensive Python-based system for macromolecular structure solution. Acta Crystallogr. D. Biol. Crystallogr. 66:213-221). Fo-Fc maps were calculated using PHENIX, and coordinates for CEM-101 were placed into this unbiased difference density using the software Coot (Emsley, P., and K. Cowtan. 2004. Coot: model-building tools for molecular graphics. Acta Crystallogr. D. Biol. Crystallogr. 60:2126-2132). Individual atomic displacement parameter values for the comparison between CEM-101 and telithromcyin were calculated using PHENIX. Figures were made using PyMol.

Example

Affinity of CEM-101 to wild-type ribosomes from *E. coli* and *S. aureus*. Binding of CEM-101 to wild-type ribosomes from Gram-negative and Gram-positive bacteria was initially analyzed by competition with [$^{14}$C]erythromycin. For that, the binding of radiolabeled erythromycin to the preparations of *E. coli* and *S. aureus* 70S ribosomes was first analyzed. In saturation binding experiments, [$^{14}$C]erythromycin readily bound to ribosomes from both bacteria, exhibiting Kd of 66±11 nM and 11±1 nM for the *E. coli* and *S. aureus* ribosomes, respectively (data not shown). These values were comparable to those previously published ($10^{-8}$-$10^{-7}$ M) (Douthwaite, S., and C. Aagaard. 1993. Erythromycin binding is reduced in ribosomes with conformational alterations in the 23S rRNA peptidyl transferase loop. J. Mol. Biol. 232:725-731; Karahalios, P., D. L. Kalpaxis, H. Fu, L. Katz, D. N. Wilson, and G. P. Dinos. 2006. On the mechanism of action of 9-O-arylalkyloxime derivatives of 6-O-mycaminosyltylonolide, a new class of 16-membered macrolide antibiotics. Mol. Pharmacol. 70:1271-1280). Binding of erythromycin saturated close to 1 pmol of the drug per 1 pmol of *E. coli* or *S. aureus* ribosomes, indicating that the majority of the ribosomes in the preparation were competent for binding.

In competition binding experiments, CEM-101 readily displaced erythromycin from both types of ribosomes with $IC_{50}$ of 155±8 nM for the *E. coli* ribosome, and 117±3 nM for the *S. aureus* ribosome resulting in CEM-101 Kd of 62±3 nM (*E. coli*) and 12±1 nM (*S. aureus*) (Table 1). The affinity of radiolabeled [$^{14}$C]CEM-101 for *S. aureus* wild-type ribosomes was measured by saturation binding experiments. A Kd of 50±13 nM obtained with this approach was similar to that obtained by competition with erythromycin. Altogether, drug binding studies demonstrated that CEM-101 interacts with the ribosomal site that either coincides or overlaps with that of erythromycin and demonstrated that the drug binds to ribosomes of Gram-positive and Gram-negative bacteria with affinities similar to those of other macrolides.

Example

Inhibition of bacterial protein synthesis by CEM-101. The effect of CEM-101 upon bacterial protein synthesis was assayed in an *E. coli* cell-free transcription-translation system. CEM-101 inhibited the synthesis of firefly luciferase (Lux) with an $IC_{50}$ of 1.1 µM, comparable to inhibition afforded by azithromycin ($IC_{50}$ 0.3 µM) and telithromycin ($IC_{50}$ 0.5 µM). The specific effect of CEM-101 upon translation rather than transcription in the cell-free system was independently verified by using lux mRNA instead of DNA as a template (data not shown). It should be noted that the concentration of ribosomes in the bacterial cell-free translation system (600 nM) significantly exceeds the $K_d$ values of macrolide antibiotics. Therefore, $IC_{50}$ values do not accurately describe the relative efficiency of tested macrolide antibiotics in inhibition of bacterial translation, but rather provide a qualitative indication of their ability to readily interfere with the bacterial protein synthesis. In contrast to its effect upon the bacterial translation, CEM-101 showed no effect on the synthesis of luciferase in the eukaryotic (rabbit) cell-free translation system at concentrations up to 50 µM. Thus, CEM-101 exhibits selective and efficient inhibition of bacterial translation.

Example

Interaction of CEM-101 with the *E. coli* ribosome in a crystalline state. The high-resolution X-ray crystallograpic structure of the *E. coli* ribosome with bound CEM-101 was obtained (Table 2).

TABLE 2

Diffraction statistics for crystals of E. coli 70S ribosome complexed with CEM-101.

| Data collection [a] | |
|---|---|
| Space group | $P2_12_12_1$ |
| Cell dimensions | |
| a, b, c (Å) | 210.7, 433.2, 618.8 |
| a, b, g (°) | 90, 90, 90 |
| Resolution (Å) | 100-3.11 (3.17-3.11) [b] |
| $R_{sym}$ or $R_{merge}$ | 11.1 (89.9) |
| I/ σ(I) | 8.27 (1.19) |
| Completeness (%) | 93.8 (85.3) |
| Redundancy | 3.3 (2.5) |
| Refinement | |
| Resolution (Å) | 69.7-3.10 |
| No. reflections | 821, 883 |
| $R_{work}/R_{free}$ | 0.22/0.26 |
| No. atoms | 284, 555 |
| R.m.s. deviations | |
| Bond lengths (Å) | 0.006 |
| Bond angles (°) | 1.452 | a) Two crystals were used.
b) Values in parentheses are for highest-resolution shell.

The binding of telithromycin was previously studied by X-ray crystallography (Berisio, R., J. Harms, F. Schluenzen, R. Zarivach, H. A. Hansen, P. Fucini, and A. Yonath. 2003. Structural insight into the antibiotic action of telithromycin against resistant mutants. J. Bacteriol. 185:4276-4279; Tu, D., G. Blaha, P. B. Moore, and T. A. Steitz. 2005. Structures of MLSBK antibiotics bound to mutated large ribosomal subunits provide a structural explanation for resistance. Cell 121:257-270).

The binding of the fluoroketolide CEM-101, in which the 11-N side chain is a 4-[4-(3-aminophenyl)[1,2,3]triazol-1-yl]butyl group, was compared with the binding of the (non-fluoro) ketolide telithromycin, in which the 11-N side chain is a 4-[4-(3-pyridinyl)-imidazol-1-yl]butyl group. The general pose of CEM-101 in the ribosome is similar to that seen for telithromycin bound to the ribosome of *E. coli*. The placement and configuration of the lactone ring and desosamine sugar of the two drugs are essentially indistinguishable. The aminophenyltriazole head of the side chain of CEM-101 makes a similar stacking interaction with the A752-U2609 base pair as the pyridinylimidazole moiety of telithromycin; it is located at a distance of 3.5 Å from the A752 and U2609 bases and oriented parallel to them. Importantly, the interactions of the CEM-101 (and telithromycin) 11-N side chains observed in the *E. coli* ribosome are principally different from those seen previously in crystallographic complexes of ketolides with the ribosomes of *D. radiodurans* or *H. marismortui* (Berisio, R., J. Harms, F. Schluenzen, R. Zarivach, H. A. Hansen, P. Fucini, and A. Yonath. 2003. Structural insight into the antibiotic action of telithromycin against resistant mutants. J. Bacteriol. 185: 4276-4279; Schlunzen, F., J. M. Harms, F. Franceschi, H. A. Hansen, H. Bartels, R. Zarivach, and A. Yonath. 2003. Structural basis for the antibiotic activity of ketolides and azalides. Structure 11:329-338; Tu, D., G. Blaha, P. B. Moore, and T. A. Steitz. 2005. Structures of MLSBK antibiotics bound to mutated large ribosomal subunits provide a structural explanation for resistance. Cell 121:257-270). The presence of the A752-U2609 base pair in the ribosomes of *E. coli* and many pathogenic bacteria may account for this specific mode of interaction of the ketolides' side chain. Because of the 23S rRNA sequence differences, formation of such a base pair is impossible in either *D. radiodurans* or *H. marismortui*. Accordingly, the structures of ketolides complexed with the *E. coli* ribosome likely more accurately reflect interactions of the drugs with the ribosome of pathogenic bacteria.

Despite a generally similar orientation of the side chains of CEM-101 and telithromycin, the variation in their chemical structures results in an important difference in the mode of binding. The atomic displacement parameter (ADP) refinement for the CEM-101 atoms shows that the extended arm of CEM-101 exhibits a significantly lower ADP value compared with the side chain of telithromycin, whereas the average ADP values for all the other antibiotic atoms are very similar in both cases. This difference, which reflects better anchoring of CEM-101 in its binding site in the ribosome, likely results from additional hydrogen bonding interactions of the exocyclic amino group of the aminophenyl in the side chain of CEM-101. Specifically, the amino group appears to serve as a H-bond donor to O4' of A752 and 06 of G748, while it is an H-bond acceptor from N1 of G748. None of these interactions is possible for telithromycin.

A distinctive feature of CEM-101 compared to telithromycin and several other ketolides is the presence of a fluorine atom at the C2 position of the lactone ring. In the structure of CEM-101 bound to the *E. coli* ribosome, the fluorine atom is positioned at a distance of 2.7 Å from the glycosidic bond (atom N1) of C2611 and thus, can potentially contribute to the drug binding. Although some reports questioned the importance of 2-F for the activity of ketolides (Keyes, R. F., J. J. Carter, E. E. Englund, M. M. Daly, G. G. Stone, A. M. Nilius, and Z. Ma. 2003. Synthesis and antibacterial activity of 6-O-arylbutynyl ketolides with improved activity against some key erythromycin-resistant pathogens. J. Med. Chem. 46:1795-1798), comparison of the MIC values of CEM-101 with those of its analog that lacked the fluorine atom showed that CEM-101 more readily inhibited growth of streptococci carrying the erm methyltransferase gene (Table 3). Thus, fluorination of the C2 carbon atom may specifically contribute to a tighter binding of the drug to the ribosome dimethylated at A2058. In the structure of CEM-101 complexed to the *E. coli* ribosome, fluorine atom is positioned at 2.7 Å from N1 of C2611.

TABLE 3

The role of 2-fluorine atom on activity of CEM-101 against streptococci.

| Species and phenotype [a] | # of strains | CEM-101 MIC$_{50}$ | CEM-101 MIC$_{90}$ | CEM-Des-F [b] MIC$_{50}$ | CEM-Des-F [b] MIC$_{90}$ |
|---|---|---|---|---|---|
| *Streptococcus pneumoniae* Pen$^S$, Tel$^S$, Mac$^S$ | 10 | 0.03 [c] | 0.03 | 0.03 | 0.03 |
| *Streptococcus pneumoniae* Pen$^R$, Tel$^{I/R}$, Mac$^R$ | 12 [d] | 0.5 | 0.5 | 4 | 4 |
| *Streptococcus pyogenes* Tel$^S$, Mac$^S$ | 10 | 0.03 | 0.03 | 0.03 | 0.03 |
| *Streptococcus pyogenes* Tel$^R$, Mac$^R$ | 9 [e] | 0.125 | 0.25 | 2 | 2 |

[a] Clinical isolates differing in their penicillin (Pen), telithromycin (Tel) and macrolide (Mac) susceptibility. Number of strains used in the study is shown in brackets.
[b] CEM-Des-F, a derivative of CEM-101 lacking fluorine atom; Tel, telithromycin; Azt, azithromycin.
[c] MIC$_{50}$ and MIC$_{90}$ values correspond to the concentration of antibiotic (μg/mL) that inhibited 50% (MIC$_{50}$) or 90% (MIC$_{90}$) of the strains tested.
[d] All the Mac$^R$ strains of *S. pneumoniae* carried constitutive ermB gene.
[e] Eight Mac$^R$ strains of *S. pyogenes* carried constitutive ermB gene and one strain carried constitutive ermA gene.

Example

Interactions of CEM-101 with wild-type *E. coli* and *S. aureus* ribosomes in solution. Because the binding of the drug to the ribosome in the crystalline state may differ from that in solution and because biochemical, genetic, and crystallographic evidence indicates that the same compound may exhibit different interactions with the ribosomes of different species (Bottger, E. C. 2006. The ribosome as a drug target. Trends Biotechnol. 24:145-147), the question of whether the crystallographic structure of CEM-101 bound to the *E. coli* ribosome accurately reflects the drug's interactions with ribosomes of Gram-positive pathogens was explored by expanding the structural studies of CEM-101 binding by probing its interactions with the *E. coli* and *S. aureus* ribosomes using RNA footprinting (Moazed, D., and H. F. Noller. 1987. Chloramphenicol, erythromycin, carbomycin and vernamycin B protect overlapping sites in the peptidyl transferase region of 23S ribosomal RNA. Biochimie 69:879-884). Also included in this study was a C3-cladinose cousin of CEM-101, CEM-103, which lacks the C2-linked fluorine atom.

Similar to other investigated macrolides and ketolides, CEM-101 and CEM-103 protect A2058 and A2059 in domain V of 23S rRNA from modification with DMS. As can be inferred from the crystallographic structure, these protections are afforded by C5 desosamine sugar, which closely approaches the cleft formed by A2058 and A2059 residues. Furthermore, in excellent agreement with crystallographic structures of CEM-101 (and telithromycin) complexed with the *E. coli* ribosome, CEM-101, as well as telithromycin and CEM-103, strongly protects A752 from DMS modification both in *E. coli* and in *S. aureus* ribosomes. In contrast, erythromycin, which lacks the extended side chain, fails to protect A752 from DMS modification. Thus, the interaction of the CEM-101 side chain with the A752-U2609 base pair seen in the crystalline state appears to accurately reflect binding of the drug to the ribosome in solution. The lack of a C2 fluorine or the presence of a C3 cladinose in CEM-103 does not bring about any difference in the footprinting pattern, confirming that these moieties of the drug do not make contacts with rRNA residues accessible for DMS modification.

Importantly, the footprinting pattern of CEM-101 in the ribosome of *E. coli* is indistinguishable from that in the ribosome of *S. aureus*, indicating that the high-resolution structure of CEM-101 complexed to the *E. coli* ribosome described herein likely accurately reflects binding of the drug to the ribosomes of Gram-positive pathogens.

Example

Interaction of CEM-101 with *S. aureus* ribosomes dimethylated at A2058 by Erm-methyltransferase. Erm-methyltransferase modifies A2058 in 23S rRNA by consecutively adding two methyl groups to the exocyclic amino group of the adenine base. Such modification completely blocks binding of erythromycin and similar macrolides, whereas its effect on binding of ketolides is less clear (Douthwaite, S., L. H. Hansen, and P. Mauvais. 2000. Macrolide-ketolide inhibition of MLS-resistant ribosomes is improved by alternative drug interaction with domain R of 23S rRNA. Mol. Microbiol. 36:183-193; Liu, M., and S. Douthwaite. 2002. Activity of the ketolide telithromycin is refractory to Erm monomethylation of bacterial rRNA. Antimicrob. Agents Chemother. 46:1629-1633). Therefore, interaction of CEM-101 with the ribosomes isolated from a clinical *S. aureus* strain N315, which carries five chromosomal copies of constitutively expressed ermA gene present in the Tn554 transposon (Kuroda, M., T. Ohta, I. Uchiyama, T. Baba, H. Yuzawa, I. Kobayashi, L. Cui, A. Oguchi, K. Aoki, Y. Nagai, J. Lian, T. Ito, M. Kanamori, H. Matsumaru, A. Maruyama, H. Murakami, A. Hosoyama, Y. Mizutani-Ui, N. K. Takahashi, T. Sawano, R. Inoue, C. Kaito, K. Sekimizu, H. Hirakawa, S. Kuhara, S. Goto, J. Yabuzaki, M. Kanehisa, A. Yamashita, K. Oshima, K. Furuya, C. Yoshino, T. Shiba, M. Hattori, N. Ogasawara, H. Hayashi, and K. Hiramatsu. 2001. Whole genome sequencing of meticillin-resistant *Staphylococcus aureacs*. Lancet 357:1225-1240) was investigated. The ribosomes isolated from the *S. aureus* N315 strain are extensively dimethylated at the A2058 residue, which agrees well with the lack of binding of [$^{14}$C]erythromycin to ribosomes prepared from this strain (data not shown).

Footprinting analysis was used to test interactions of ketolides (CEM-101 and telithromycin) and cladinose-containing macrolides (CEM-103 and erythromycin) with the 2058-dimethylated ribosomes isolated from the *S. aureus* N315 strain. Ribosomes were incubated with the drugs (present at 100 μM concentration) and probed by DMS modification. Because dimethylated A2058 blocks progression of reverse transcriptase along the RNA template, a strong reverse transcriptase stop is observed at A2058 on the primer extension gel (Vester, B., and S. Douthwaite. 1994. Domain V of 23S rRNA contains all the structural elements necessary for recognition by the ErmE methyltransferase. J. Bacteriol. 176:6999-7004; Zhong, P., Z. Cao, R. Hammond, Y. Chen, J. Beyer, V. D. Shortridge, L. Y. Phan, S. Pratt, J. Capobianco, K. A. Reich, R. K. Flamm, Y. S. Or, and L. Katz. 1999. Induction of ribosome methylation in MLS-resistant *Streptococcus pneumoniae* by macrolides and ketolides. Microb. Drug Resist. 5:183-188). Therefore, it is impossible to use footprinting to evaluate interactions of macrolides with this position in the *S. aureus* N315 ribosomes. However, examination of the intensity of the A2059 band clearly showed that both CEM-101 and CEM-103, but not erythromycin, could bind to the Erin-modified ribosome, resulting in protection of A2059 from DMS modification. Telithromycin also protected A2059 but to a lesser extent than CEM-101 or CEM-103. For a more extensive analysis of binding of ketolides and CEM-103 to the *S. aureus* ribosome, footprinting studies were extended by including two more modifying reagents, kethoxal, which modifies guanosines, and 1-cyclohexyl-3-(2-morpholinoethyl)-carbodiimide metho-p-toluene sulfonate (CMCT), which modifies uridines (Merryman, C., and H. F. Noller. 1998. Footprinting and modification-interference analysis of binding sites on RNA, p. 237-253. In C. W. J. Smith (ed.), RNA:Protein Interactions, A Practical Approach. Oxford University Press, Oxford). Kethoxal probing showed that CEM-101 and CEM-103 partially protected G2505 from kethoxal modification and fully protected U2609 from modification with CMCT. Telithromycin afforded a notably weaker protection at both positions. Erythromycin did not protect either of the two positions, consistent with the fact that dimethylation of A2058 is known to prevent erythromycin binding (Weisblum, B. 1995. Erythromycin resistance by ribosome modification. Antimicrob. Agents Chemother. 39:577-585).

The overall conclusion that can be drawn from the results of the footprinting studies is that macrolides with the extended alkyl side chain bearing a (hetero)aryl group, when present at a sufficiently high concentration, can bind to the ribosome dimethylated at A2058 by the action of Erm methyltransferase. It is also apparent that the side chains of CEM-101 and CEM-103, characterized by the triazole moiety and by the aminophenyl moiety and its apparent additional interaction with the A752-U2609 base pair, exhibit more efficient binding compared with telithromycin.

Example

Screening results using conventional screens as indicated with new macrolide agents are provided in the following tables.

| Organism | CEM-219 | CEM-199 |
|---|---|---|
| *S. pneumoniae* | | |
| ATCC 49619/WT | ≤0.015 | 0.06 |
| 117-20B/WT | ≤0.015 | 0.06 |
| 014-4331A/mefA | 0.5 | 1 |
| 007-4589A/ermB | ≤0.015 | 0.12 |
| 120-1037B/- ermB/mefA | 0.12 | 0.5 |
| *S. pyogenes* | | |
| ATCC 19615 | ≤0.015 | 0.06 |
| 129-7129A/ermA | ≤0.015 | 0.12 |
| 089-14217A/ermB | 0.5 | 1 |
| *S. aureus* | | |
| 024-11A/WT | 0.5 | 0.5 |
| ATCC 29213/WT | 0.25 | 0.5 |
| BAA-977/ermA | 0.25 | 0.5 |
| D-5/ermA | >16 | >16 |
| *M. luteus* | | |
| ATCC 9341/WT | ≤0.015 | 0.06 |
| *E. coli* | | |
| ATCC 25922/WT | >16 | 16 |
| 122-5930A/WT | >16 | 16 |

Example. Preparation of New Macrolide Agents

The new macrolide agents can be prepared using methods which are analogous to methods known in the art for the preparation of macrocyles and the substituents or by methods described herein. The following examples further illustrate specific embodiments of the invention; however, the following illustrative examples should not be interpreted in any way to limit the invention. Abbreviations used in the examples include the following: DCM, dichloromethane; DMAP, 4-dimethylaminopyridine; DMSO; dimethyl sulfoxide; EA, ethyl acetate; $^1$H-NMR, proton nuclear magnetic resonance spectroscopy; MeOH, methanol; Mw, molecular Example. Preparation 1. Clarithromycin Dibenzoate a. Synthesis of erythromycin A 9-oxime (1). A mixture of erythromycin A (15 g, 20.4 mmol), $NH_2OH \cdot HCl$ (7.3 g, 105 mmol) and triethylamine (7 g, 69 mmol) in MeOH (23 mL) was heated to reflux overnight. A white solid formed during the reaction. The reaction mixture was concentrated to a small volume. To the obtained residue was added dilute aqueous $NH_4OH$ solution at 0° C. until the pH of the mixture reached about 10 to 11. Additional solid precipitated out from the mixture during this process. The mixture was filtered, the collected solid was washed with water and dried under vacuum to give 14.2 g of 1 as white granular solid in 93% yield. TLC analysis ($DCM:MeOH:NH_4OH=90:10:1$) of the obtained 1 showed very slight contamination of a lower spot which can be attributed to the Z-isomer. Mass analysis of the obtained 1 showed a peak with molecular weight (Mw of 749) of the desired product as the prominent peak. $^1$H-NMR analysis of the product showed it was a mixture of the desired 1 and the HCl salt of the desired 1. The crude product was used for the next step reaction without purification.

b. Synthesis of O-(2-methoxy-2-propyl)erythromycin A 9-oxime (2). To a solution of 1 (3 g, 4 mmol) in anhydrous dichloromethane (DCM, 21 mL) was added 2-methoxypropene (1.5 g, 20.8 mmol), followed by pyridine hydrochloride (0.72 g, 6.2 mmol) at 0° C. After the addition, the reaction mixture was stirred at 0° C. at RT for 30 min. TLC analysis of the reaction mixture ($DCM:MeOH:NH_4OH=90:10:1$) showed only a small amount of product formed with large amount of unreacted 1 remaining. The reaction mixture was cooled back to 0° C. To this was added another 0.5 g of 2-methoxypropene (6.9 mmol). The mixture was stirred at 0° C. for another 0.5 h. TLC analysis of the reaction mixture still showed an incomplete reaction. Therefore, another 0.5 g of 2-methoxypropene (6.9 mmol), followed with another 0.1 g of pyridine hydrochloride (0.86 mmol) was added to the reaction mixture at 0° C. The reaction mixture was stirred at 0° C. for another 15 min. TLC analysis of the reaction mixture showed the absence of starting material. The reaction mixture was diluted with saturated aqueous $NaHCO_3$ solution. The DCM layer was separated and the aqueous layer was extracted with DCM. The combined DCM layers were washed with brine, dried over $MgSO_4$, concentrated to dryness to give 3.3 g crude product as a white foam in quantitative yield. Mass analysis of the crude 2 showed the desired product peak as the major peak (Mw of 821) along with a very minor peak with molecular weight of 861 which was attributed to an over-reacted side-product. $^1$H-NMR of the crude 2 showed the desired structure of 2 along with the contamination of the possible 2-methoxypropan-2-ol and pyridine. This crude product was used for the next step reaction without further purification.

c. Synthesis of 2',4"-dibenzoyl-O-(2-methoxy-2-propyl) erythromycin A 9-oxime (3). To a solution of 2 (4.1 g, 5 mmol) in ethyl acetate (65 mL) was added benzoic anhydride (4.5 g, 20 mmol), followed with triethylamine (1.26 g, 12.5 mmol) and DMAP (0.9 g, 7.4 mmol) at RT. The resulting mixture was stirred at RT for 36 h. The reaction mixture was diluted with saturated aqueous $NaHCO_3$ solution. The EA layer was separated and the aqueous layer was extracted with EA. The combined EA layers were washed with brine, dried over $MgSO_4$, filtered to remove the drying agent, and concentrated to dryness. The obtained residue was subjected to silica gel column chromatography ($DCM:MeOH:NH_4OH=97:3:0.3$) to give 4.2 g of 3 in 80% yield as a white solid. Mass analysis of the obtained 3 showed the peak with molecular weight (Mw of 1029) of the desired product as the major component peak. $^1$H-NMR analysis of the obtained 3 showed the structure of the named product.

d. Synthesis of 2',4"-dibenzoyl-O-(2-methoxy-2-propyl)-6-O-methyl-erythromycin A 9-oxime (4). A solution of 3 (3.8 g, 3.7 mmol) in anhydrous THF (15 mL) and anhydrous DMSO (15 mL) was cooled to 0° C. To this was added powdered KOH (0.46 g, 8.2 mmol), followed with methyl iodide (1.06 g, 7.5 mmol) at 0° C. The resulting reaction mixture was stirred at 0° C. for 5 min. It turned to a thick paste which stopped the stirring. The mixture was warmed to RT for 5 min and the mixture remained a thick paste. Therefore, another 15 mL of THF and 15 mL of DMSO was added to the reaction mixture. After the addition, the reaction mixture turned to a free flowing suspension. The mixture was stirred at RT for another 0.5 hr, diluted with saturated aqueous $NaHCO_3$ solution, extracted with ethyl acetate. The ethyl acetate extract was washed with brine, dried over $MgSO_4$ and concentrated to dryness. The obtained residue was subjected to silica gel column chromatography ($DCM:MeOH:NH_4OH=97:3:0.3$) to give 2.83 g of 4 as a white solid in 73% yield. Mass analysis of isolated 4 showed the desired product peak (Mw of 1043) as the major component along with a minor peak of Mw 1057 which has the mass of an over-methylated side-product. $^1$H-NMR analysis of isolated 4 is consistent with the structure of the named product.

e. Synthesis of Clarithromycin Dibenzoate [2',4"-dibenzoyl-6-O-methyl-erythromycin A]. To a solution of 4 (800 mg, 0.78 mmol) in ethanol (8 mL) and water (8 mL) was added sodium metabisulfite (740 mg, 3.89 mmol) at RT. The pH of the resulting mixture was adjusted to 2-3 with the addition of formic acid (1.5 mL). The mixture was heated at 60° C. for 1 h. Mass analysis of the reaction mixture showed a minor amount of the product along with large amount of the deprotected oxime intermediate (Mw of 971). To the reaction mixture was added another 2 g of sodium metabisulfite (10.5 mmol). The mixture was stirred at 60° C. for another 7 h, then cooled to RT. A white solid precipitated out from the reaction mixture as the reaction progressed. The reaction mixture was neutralized with dilute aqueous $NaHCO_3$ solution until pH of 8-9 and the resultant mixture was filtered. The collected white solid was dried under vacuum to give 760 mg of clarithromycin dibenzoate. This crude product was combined with the crude product obtained from a pilot run at 200 mg of 11 scale and subjected to silica gel column chromatography to give 730 mg of clarithromycin dibenzoate in 79% yield. Mass analysis of the purified product showed the desired product peak (Mw of 956) as the major component along with a minor peak with Mw of 970 which was attributed to the C-11 hydroxy methylated impurity carried over from the prior step. $^1$H-NMR analysis of the purified product showed the desired structure of clarithromycin dibenzoate.

Example. Preparation 2

11-N-(4-Azidobutyl)-5-O-(2'-benzoyldesosaminyl)-6-O-methyl-3-oxo-erythronolide A 11,12-cyclic carbamate. The azide may be obtained from clarithromycin dibenzoate using a procedure described in WO 2009/055557 A1 (US 2010-0216731 A1) at Example 5 or Example 5A, and the preceding examples.

Example. Preparation 3

11-N-(4-Azidobutyl)-5-O-(2'-benzoyldesosaminyl)-2-fluoro-6-O-methyl-3-oxo-erythronolide A 11,12-cyclic carbamate. The azide may be obtained from clarithromycin dibenzoate using a procedure described in WO 2009/055557 A1 (US 2010-0216731 A1) at Example 6 or Example 6B, and the preceding examples.

Example. Comparison Example 1

Synthesis of 11-N-[4-[4-(3-aminophenyl)[1,2,3]triazol-1-yl]butyl]-6-O-methylerythromycin A 11,12-cyclic carbamate (CEM-103). The compound may be prepared from 2',4"-di-O-benzoyl-1'-N-(4-azidobutyl)-6-O-methylerythromycin A 11,12-cyclic carbamate, Example 3 of WO 2009/055557, using methods analogous to those described for the preparation of CEM-101.

Example. Comparison Example 2

Synthesis of 11-N-[4-[4-(3-aminophenyl)[1,2,3]triazol-1-yl]butyl]-5-O-desosaminyl-6-O-methyl-3-oxo-erythronolide A 11,12-cyclic carbamate (Desfluoro CEM-101, CEM-Des-F). The compound may be prepared from the azide of Preparation 2, above, using methods analogous to those described for the preparation of CEM-101.

Example. Comparison Example 3

Synthesis of 5-O-desosaminyl-11-N-[4-[4-(indol-3-ylmethyl)[1,2,3]triazol-1-yl]butyl]-6-O-methyl-3-oxo-erythronolide A 11,12-cyclic carbamate (CEM-199). Molecular formula: $C_{46}H_{68}N_6O_{10}$; Exact Mass: 864.50; Mol. Wt.: 865.07.

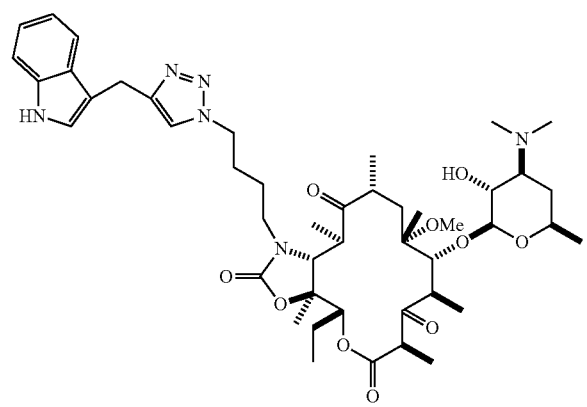

The compound may be prepared from the azide of Preparation 2, above, using methods analogous to those described for the preparation of CEM-101.

Example

Synthesis of 2-fluoro-5-O-desosaminyl-11-N-[4-[4-(indol-3-ylmethyl)[1,2,3]triazol-1-yl]butyl]-6-O-methyl-3-oxo-erythronolide A 11,12-cyclic carbamate (CEM-219). Molecular formula: $C_{46}H_{67}FN_6O_{10}$; Exact Mass: 882.49; Mol. Wt.: 883.06.

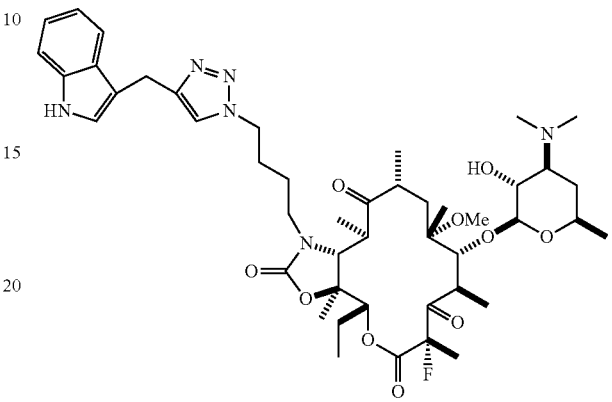

The compound may be prepared from the azide of Preparation 3, above, using methods analogous to those described for the preparation of CEM-101.

What is claimed is:
1. A compound of formula I,

$$A\text{-}L\text{-}Q \qquad (I)$$

or a pharmaceutically acceptable salt thereof, wherein:
A indazolyl, or benzimidazolinyl, each of which is optionally substituted;
L is $X_a$—$Y_b$—$Z_c$;
a, b and c are each independently 0 or 1, provided at least one of a, b and c is 1;
X is $CH_2R^aR^b$, O, S or $NR^c$;
Y is an optionally substituted triazolyl;
Z is $(CH_2)_m$; where m is 1, 2, 3 or 4; and each of said $CH_2$ groups is independently optionally substituted with one or two methyl groups or replaced with O, S or $NR^d$; and
$R^a$, $R^b$, $R^c$ and $R^d$ are each independently H or $CH_3$;
Q is

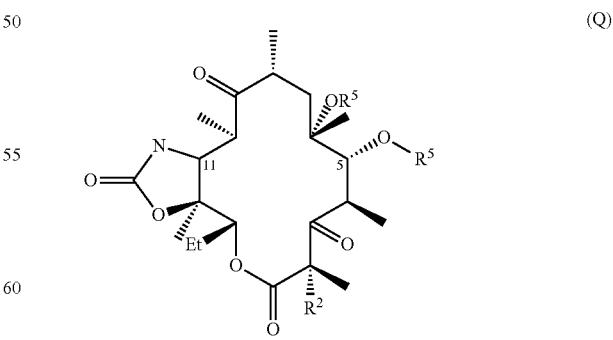

(Q)

in which L is bonded to the 11-N of Q;
$R^2$ is H or F;
$R^5$ is an aminosaccharide residue; and
$R^6$ is H or (1-6C)alkyl.

2. The compound or salt of claim 1 wherein $R^2$ is F.

3. The compound or salt of claim 1 wherein $R^5$ is an optionally substituted desosaminyl.

4. The compound or salt of claim 1 wherein $R^6$ is methyl.

5. A compound of the formula

A-L-Q or a salt thereof, wherein
A is 3-indolyl
L is $X_a$—$Y_b$—$Z_c$;
a, b and c are each independently 0 or 1, provided at least one of a, b and c is 1;
X is $CH_2R^aR^b$, O, S or $NR^c$;
Y is an optionally substituted triazolyl;
Z is $(CH_2)_m$; where m is 1, 2, 3 or 4; and each of said $CH_2$ groups is independently optionally substituted with one or two methyl groups or replaced with O, S or $NR^d$; and
$R^a$, $R^b$, $R^c$ and $R^d$ are each independently H or $CH_3$;
Q is

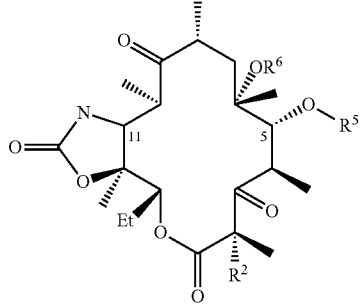

(Q)

where L is bonded to the 11-N of Q;
$R^2$ is H or F;
$R^5$ is an aminosaccharide residue; and
$R^6$ is H or (1-6C)alkyl.

6. The compound or salt of claim 1 wherein Z is —$(CH_2)_4$—, —$(CH_2)_3$—O—, —$(CH_2)_3$—NH—, —$(CH_2)_3$—, —$(CH_2)_2$—O—, —$(CH_2)_2$—NH—, or —$(CH_2)_2$—.

7. A pharmaceutical composition comprising the compound or salt of claim 1 and further comprising at least one pharmaceutically acceptable carrier or excipient.

8. A method of treatment of a bacterial infection, a protozoal infection, or a disorder related to a bacterial infection or protozoal infection comprising the step of administering to a subject in need thereof a therapeutically effective amount of the compound or salt of claim 1.

9. A compound of the formula

A-X—Y—Z-Q or a salt thereof, wherein
A-X—Y is selected from the group consisting of

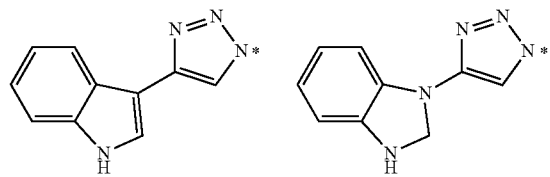

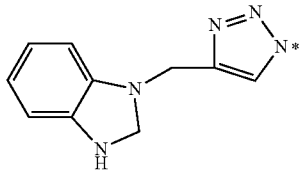

-continued

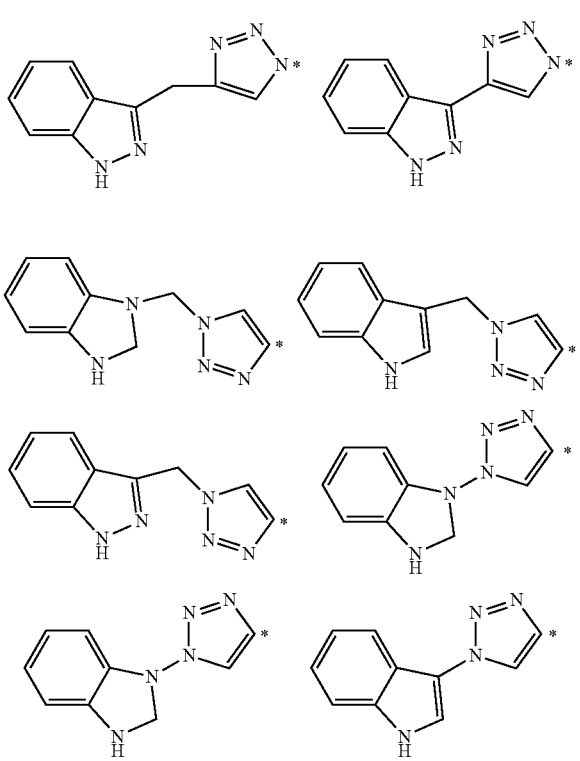

Z is $(CH_2)_m$; where m is 1, 2, 3 or 4; and each of said $CH_2$ groups is independently optionally substituted with one or two methyl groups or replaced with O, S or $NR^d$; and
$R^d$ is independently H or $CH_3$;

Q is

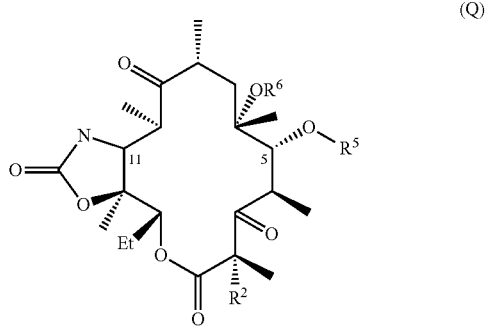

(Q)

where A-X—Y—Z is bonded to the 11-N of Q;
$R^2$ is H or F;
$R^5$ is an aminosaccharide residue; and
$R^6$ is H or (1-6C)alkyl.

10. The compound of claim 9 of the formula

[chemical structure]

or a pharmaceutically acceptable salt thereof.

11. The compound of claim 9 of the formula

[chemical structure]

12. The compound of claim 9 of the formula

[chemical structure]

or a pharmaceutically acceptable salt thereof.

13. The compound of claim 9 of the formula

[chemical structure]

14. The compound or salt of claim 1 wherein $R^5$ is desosaminyl.

15. The compound or salt of claim 1 wherein Z is $(CH_2)_4$, $(CH_2)_3$—O, $(CH_2)_3$—NH, $(CH_2)_3$, —$(CH_2)_2$—O, or $(CH_2)_2$—NH.

16. The compound or salt of claim 5 wherein $R^2$ is F.

17. The compound or salt of claim 5 wherein $R^5$ is an optionally substituted desosaminyl.

18. The compound or salt of claim 5 wherein $R^5$ is desosaminyl.

19. The compound or salt of claim 5 wherein $R^6$ is methyl.

20. The compound or salt of claim 5 wherein Z is $(CH_2)_4$, $(CH_2)_3$—O, $(CH_2)_3$—NH, $(CH_2)_3$, $(CH_2)_2$—O, $(CH_2)_2$—NH, or $(CH_2)_2$.

21. The compound or salt of claim 5 wherein Z is $(CH_2)_4$.

22. A pharmaceutical composition comprising the compound or salt of claim 5 and further comprising at least one pharmaceutically acceptable carrier or excipient.

23. A method of treatment of a bacterial infection, a protozoal infection, or a disorder related to a bacterial infection or protozoal infection comprising the step of administering to a subject in need thereof a therapeutically effective amount of the compound or salt of claim 5.

24. The compound or salt of claim 9 wherein $R^2$ is F.

25. The compound or salt of claim 9 wherein $R^5$ is an optionally substituted desosaminyl.

26. The compound or salt of claim 9 wherein $R^5$ is desosaminyl.

27. The compound or salt of claim 9 wherein $R^6$ is methyl.

28. The compound or salt of claim 9 wherein Z is $(CH_2)_4$, $(CH_2)_3$—O, $(CH_2)_3$—NH, $(CH_2)_3$, $(CH_2)_2$—O, $(CH_2)_2$—NH, or $(CH_2)_2$.

29. The compound or salt of claim 9 wherein Z is $(CH_2)_4$.

30. A pharmaceutical composition comprising the compound or salt of claim 5 and further comprising at least one pharmaceutically acceptable carrier or excipient.

31. A method of treatment of a bacterial infection, a protozoal infection, or a disorder related to a bacterial infection or protozoal infection comprising the step of administering to a subject in need thereof a therapeutically effective amount of the compound or salt of claim 9.

* * * * *